(12) United States Patent
Bourinet et al.

(10) Patent No.: US 8,664,179 B2
(45) Date of Patent: Mar. 4, 2014

(54) IDENTIFICATION OF NOVEL ANTAGONIST TOXINS OF T-TYPE CALCIUM CHANNEL FOR ANALGESIC PURPOSES

(75) Inventors: Emmanuel Bourinet, Saint Mathieu de Treviers (FR); Pierre Escoubas, Valbonne (FR); Fabrice Marger, Saint-Jean de Vedas (FR); Joel Nargeot, Montpellier (FR); Michel Lazdunski, Colombo (FR)

(73) Assignees: Centre National de la Recherche Scientifique (CNRS), Paris (FR); Universite de Nice Sophia Antipolis, Nice (FR)

( * ) Notice: Subject to any disclaimer, the term of this patent is extended or adjusted under 35 U.S.C. 154(b) by 0 days.

(21) Appl. No.: 13/144,734

(22) PCT Filed: Jan. 15, 2010

(86) PCT No.: PCT/FR2010/000037
§ 371 (c)(1),
(2), (4) Date: Nov. 1, 2011

(87) PCT Pub. No.: WO2010/081971
PCT Pub. Date: Jul. 22, 2010

(65) Prior Publication Data
US 2012/0040909 A1    Feb. 16, 2012

(30) Foreign Application Priority Data
Jan. 15, 2009   (FR) ...................................... 09 00174

(51) Int. Cl.
*C07K 14/00*    (2006.01)
(52) U.S. Cl.
USPC .......................... 514/17.4; 435/69.1; 530/324

(58) Field of Classification Search
None
See application file for complete search history.

(56) References Cited

U.S. PATENT DOCUMENTS 5,756,663 A    5/1998    Lampe
5,776,896 A    7/1998    Lampe

FOREIGN PATENT DOCUMENTS

JP    2002509080 A    3/2002
WO    9942480 A1    8/1999

OTHER PUBLICATIONS

Middleton et al., Two Tarantula Peptides Inhibit Activation of Multiple Sodium Channels, Dec. 17, 2002, Biochemistry 41(50);14734-14747.*
Kraus et al., "Modulation of α1G and α1C CA Channels by the Spider Toxin Protx-II", Society for Neuroscience, 2000, vol. 26, No. 1-2, Abstract No. 234.14, XP009120110.
International Search Report dated May 6, 2010, corresponding to the PCT application.
Bourinet et al., "Silencing of the Cav3.2 T-type calcium channel gene in sensory neurons demonstrates its major role in nociception", The EMBO Journal, 2005, vol. 24, No. 2, pp. 315-324.

* cited by examiner

*Primary Examiner* — John Ulm
(74) *Attorney, Agent, or Firm* — Young & Thompson

(57) ABSTRACT

A peptide with the following sequence YCQKFLWTCD-SERPCCEGLVCRLWCKIN (SEQ ID NO 1) or a derivative thereof, and nucleic acids coding for the peptide having the sequence (SEQ ID NO 1). Also the use of this peptide as an antagonist and/or reverse agonist of T-type calcium channels. A use of the peptide for preparing a drug, in particular an analgesic one.

12 Claims, 8 Drawing Sheets

Figure 5

Sequence pT7-7 :

AATTCTCATGTTTGACAGCTTATCATCGATAAGCTTGGGCTGCAGGTCGACTCTAGAGGATCCCCGGGCGCGAAT
TCTAGCCATATGTATATCTCCTTCTTAAAGTTAAACAAAATTATTTCTAGAGGGAAACCGTTGTGGTCTCCCTAT
AGTGAGTCGTATTAATTTCGAAGTCTATCAGAAGTTCGAATCGCTGGGCCTCGCGCGTTTCGGTGATGACGGTGA
AAACCTCTGACACATGCAGCTCCCGGAGACGGTCACAGCTTGTCTGTAAGCGGATGCCGGGAGCAGACAAGCCCG
TCAGGGCGCGTCAGCGGGTGTTGGCGGGTGTCGGGGCGCAGCCATGACCCAGTCACGTAGCGATAGCGGAGTGTA
TATACTGGCTTAACTATGCGGCATCAGAGCAGATTGTACTGAGAGTGCACCANAGATCTNTGCGGTGTCAAATAC
CGCACAGATGCGTAAGGAGAAAATACCGCATCAGGCGCTCTTCCGCTTCCTCGCTCACTGACTCGCTGCGCTCGG
TCGTTCGGCTGCGGCGAGCGGTATCAGCTCACTCAAACGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTGGCGTTTTTCC
ATAGGCTCCGCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCAATGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCATGAGATTATCAAAAAGGA
TCTTCACCTAGATCCTTTTAATTCTTGAAGACGAAAGGGCCTCGTGATACGCCTATTTTTATAGGTTAATGTCAT
GATAATAATGGTTTCTTAGACGTCAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAATAATATTGAAAAAGGAA
GAGTATGAGTATTCAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTACATCGAACTGGATCT
CAACAGCGGTAAGATCCTTGAGAGTTTTCGCCCCGAAGAACGTTTTCCAATGATGAGCACTTTTAAAGTTCTGCT
ATGTGGCGCGGTATTATCCCGTGTTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGTAAGAGAATTATGCAGTGCTGC
CATAACCATGAGTGATAACACTGCGGCCAACTTACTTCTGACAACGATCGGAGGACCGAAGGAGCTAACCGCTTT
TTTGCACAACATGGGGGATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTGGCGAACTACTTACTCT
AGCTTCCCGGCAACAATTAATAGACTGGATGGAGCCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTCATATATACTTTAGAT
TGATTT

Figure 6 A

```
Sequence pGex-4-T1
ACGTTATCGACTGCACGGTGCACCAATGCTTCTGGCGTCAGGCAGCCATCGGAAGCTGTGGTATGGCTGTGCAGG
TCGTAAATCACTGCATAATTCGTGTCGCTCAAGGCGCACTCCCGTTCTGGATAATGTTTTTTGCGCCGACATCAT
AACGGTTCTGGCAAATATTCTGAAATGAGCTGTTGACAATTAATCATCGGCTCGTATAATGTGTGGAATTGTGAG
CGGATAACAATTTCACACAGGAAACAGTATTCATGTCCCTATACTAGGTTATTGGAAAATTAAGGGCCTTGTGC
AACCCACTCGACTTCTTTTGGAATATCTTGAAGAAAAATATGAAGAGCATTTGTATGAGCGCGATGAAGGTGATA
AATGGCGAAACAAAAGTTTGAATTGGGTTTGGAGTTTCCCAATCTTCCTTATTATATTGATGGTGATGTTAAAT
TAACACAGTCTATGGCCATCATACGTTATATAGCTGACAAGCACAACATGTTGGGTGGTTGTCCAAAAGAGCGTG
CAGAGATTTCAATGCTTGAAGGAGCGGTTTTGGATATTAGATACGGTGTTTCGAGAATTGCATATAGTAAAGACT
TTGAAACTCTCAAAGTTGATTTTCTTAGCAAGCTACCTGAAATGCTGAAAATGTTCGAAGATCGTTTATGTCATA
AAACATATTTAAATGGTGATCATGTAACCCATCCTGACTTCATGTTGTATGACGCTCTTGATGTTGTTTTATACA
TGGACCCAATGTGCCTGGATGCGTTCCCAAAATTAGTTTGTTTTAAAAAACGTATTGAAGCTATCCCACAAATTG
ATAAGTACTTGAAATCCAGCAAGTATATAGCATGGCCTTTGCAGGGCTGGCAAGCCACGTTTGGTGGTGGCGACC
ATCCTCCAAAATCGGATCTGGTTCCGCGTGGATCCCCGGAATTCCCGGGTCGACTCGAGCGGCCGCATCGTGACT
GACTGACGATCTGCCTCGCGCGTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAGCGGGTGTTGGCGGGTGTCGGG
GCGCAGCCATGACCCAGTCACGTAGCGATAGCGGAGTGTATAATTCTTGAAGACGAAAGGGCCTCGTGATACGCC
TATTTTTATAGGTTAATGTCATGATAATAATGGTTTCTTAGACGTCAGGTGGCACTTTTCGGGGAAATGTGCGCG
GAACCCCTATTTGTTTATTTTTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGATGCTGAAGATCAGTTGGGTGCACGAG
TGGGTTACATCGAACTGGATCTCAACAGCGGTAAGATCCTTGAGAGTTTTCGCCCCGAAGAACGTTTTCCAATGA
TGAGCACTTTTAAAGTTCTGCTATGTGGCGCGGTATTATCCCGTGTTGACGCCGGGCAAGAGCAACTCGGTCGCC
GCATACACTATTCTCAGAATGACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACTTACTTCTGACAACGATCGGAG
GACCGAAGGAGCTAACCGCTTTTTTGCACAACATGGGGGATCATGTAACTCGCCTTGATCGTTGGGAACCGGAGC
TGAATGAAGCCATACCAAACGACGAGCGTGACACCACGATGCCTGCAGCAATGGCAACAACGTTGCGCAAACTAT
TAACTGGCGAACTACTTACTCTAGCTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTGGAGCCGGTGAGCGTGGGTCTCGCG
GTATCATTGCAGCACTGGGGCCAGATGGTAAGCCCTCCCGTATCGTAGTTATCTACACGACGGGGAGTCAGGCAA
CTATGGATGAACGAAATAGACAGATCGCTGAGATAGGTGCCTCACTGATTAAGCATTGGTAACTGTCAGACCAAG
TTTACTCATATATACTTTAGATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGCGCAGATACCAAATA
```

Figure 6 B

```
CTGTCCTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATAGTTAC
CGGATAAGGCGCAGCGGTCGGGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCAGGGGGGCGGAGCCTATGGAAAAACG
CCAGCAACGCGGCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAACGACCGAGCGCA
GCGAGTCAGTGAGCGAGGAAGCGGAAGAGCGCCTGATGCGGTATTTTCTCCTTACGCATCTGTGCGGTATTTCAC
ACCGCATAAATTCCGACACCATCGAATGGTGCAAAACCTTTCGCGGTATGGCATGATAGCGCCCGGAAGAGAGTC
AATTCAGGGTGGTGAATGTGAAACCAGTAACGTTATACGATGTCGCAGAGTATGCCGGTGTCTCTTATCAGACCG
TTTCCCGCGTGGTGAACCAGGCCAGCCACGTTTCTGCGAAAACGCGGGAAAAAGTGGAAGCGGCGATGGCGGAGC
TGAATTACATTCCCAACCGCGTGGCACAACAACTGGCGGGCAAACAGTCGTTGCTGATTGGCGTTGCCACCTCCA
GTCTGGCCCTGCACGCGCCGTCGCAAATTGTCGCGGCGATTAAATCTCGCGCCGATCAACTGGGTGCCAGCGTGG
TGGTGTCGATGGTAGAACGAAGCGGCGTCGAAGCCTGTAAAGCGGCGGTGCACAATCTTCTCGCGCAACGCGTCA
GTGGGCTGATCATTAACTATCCGCTGGATGACCAGGATGCCATTGCTGTGGAAGCTGCCTGCACTAATGTTCCGG
CGTTATTCTTGATGTCTCTGACCAGACACCCATCAACAGTATTATTTTCTCCCATGAAGACGGTACGCGACTGG
GCGTGGAGCATCTGGTCGCATTGGGTCACCAGCAAATCGCGCTGTTAGCGGGCCCATTAAGTTCTGTCTCGGCGC
GTCTGCGTCTGGCTGGCTGGCATAAATATCTCACTCGCAATCAAATTCAGCCGATAGCGGAACGGGAAGGCGACT
GGAGTGCCATGTCCGGTTTTCAACAAACCATGCAAATGCTGAATGAGGGCATCGTTCCCACTGCGATGCTGGTTG
CCAACGATCAGATGGCGCTGGGCGCAATGCGCGCCATTACCGAGTCCGGGCTGCGCGTTGGTGCGGATATCTCGG
TAGTGGGATACGACGATACCGAAGACAGCTCATGTTATATCCCGCCGTTAACCACCATCAAACAGGATTTTCGCC
TGCTGGGGCAAACCAGCGTGGACCGCTTGCTGCAACTCTCTCAGGGCCAGGCGGTGAAGGGCAATCAGCTGTTGC
CCGTCTCACTGGTGAAAAGAAAAACCACCCTGGCGCCCAATACGCAAACCGCCTCTCCCCGCGCGTTGGCCGATT
CATTAATGCAGCTGGCACGACAGGTTTCCCGACTGGAAAGCGGGCAGTGAGCGCAACGCAATTAATGTGAGTTAG
CTCACTCATTAGGCACCCCAGGCTTTACACTTTATGCTTCCGGCTCGTATGTTGTGTGGAATTGTGAGCGGATAA
CAATTTCACACAGGAAACAGCTATGACCATGATTACGGATTCACTGGCCGTCGTTTTACAACGTCGTGACTGGGA
AAACCCTGGCGTTACCCAACTTAATCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGCGCTTTGCCTGGTTTCCGGCACCAGA
AGCGGTGCCGGAAAGCTGGCTGGAGTGCGATCTTCCTGAGGCCGATACTGTCGTCGTCCCCTCAAACTGGCAGAT
GCACGGTTACGATGCGCCCATCTACACCAACGTAACCTATCCCATTACGGTCAATCCGCCGTTTGTTCCCACGGA
GAATCCGACGGGTTGTTACTCGCTCACATTTAATGTTGATGAAAGCTGGCTACAGGAAGGCCAGACGCGAATTAT
TTTTGATGGCGTTGGAATT
```

Figure 7 A

```
Sequence pET32
atccggatatagttcctcctttcagcaaaaaaccctcaagacccgtttagaggccccaaggggttatgctagtt
attgctcagcggtggcagcagccaactcagcttcctttcgggctttgttagcagccggatctcagtggtggtggt
ggtggtgctcgagtgcggccgcaagcttgtcgacggagctcgaattcggatccgatatcagccatggccttgtcg
tcgtcgtcggtacccagatctgggctgtccatgtgctggcgttcgaatttagcagcagcggtttctttcatacca
gaaccgcgtggcaccagaccagaagaatgatgatgatgatggtgcatatggccagaaccagaaccggccaggtta
gcgtcgaggaactctttcaactgacctttagacagtgcacccactttggttgccgccacttcaccgttttgaac
agcagcagagtcgggataccacggatgccatatttcggcgcagtgccaggggttttgatcgatgttcagttttgca
acggtcagtttgccctgatattcgtcagcgatttcatccagaatcgggcgatcattttgcacggaccgcaccac
tctgcccagaaatcgacgaggatcgcccgtccgctttgagtacatccgtgtcaaaactgtcgtcagtcaggtga
ataattttatcgctcatatgtatatctccttcttaaagttaaacaaaattatttctagaggggaattgttatccg
ctcacaattcccctatagtgagtcgtattaatttcgcgggatcgagatcgatctcgatcctctacgccggacgca
tcgtggccggcatcacggcgccacaggtgcggttgctggcgcctatatcgccgacatcaccgatggggaagatc
gggctcgccacttcgggctcatgagcgcttgtttcggcgtgggtatggtggcaggccccgtggccgggggactgt
tgggcgccatctccttgcatgcaccattccttgcggcggcggtgctcaacggcctcaacctactactgggctgct
tcctaatgcaggagtcgcataagggagagcgtcgagatcccggacaccatcgaatggcgcaaaacctttcgcggt
atggcatgatagcgcccggaagagagtcaattcaggtggtgaatgtgaaaccagtaacgttatacgatgtcgca
gagtatgccggtgtctcttatcagaccgtttcccgcgtggtgaaccaggccagccacgtttctgcgaaaacgcgg
gaaaaagtggaagcggcgatggcggagctgaattacattcccaaccgcgtggcacaacaactggcgggcaaacag
tcgttgctgattggcgttgccacctccagtctggccctgcacgcgccgtcgcaaattgtcgcggcgattaaatct
cgcgccgatcaactgggtgccagcgtggtggtgtcgatggtagaacgaagcggcgtcgaagcctgtaaagcggcg
gtgcacaatcttctcgcgcaacgcgtcagtgggctgatcattaactatccgctggatgaccaggatgccattgct
gtggaagctgcctgcactaatgttccggcgttatttcttgatgtctctgaccagacacccatcaacagtattatt
ttctcccatgaagacggtacgcgactgggcgtggagcatctggtcgcattgggtcaccagcaaatcgcgctgtta
gcgggcccattaagttctgtctcggcgcgtctgcgtctggctggctggcataaatatctcactcgcaatcaaatt
cagccgatagcggaacgggaaggcgactggagtgccatgtccggttttcaacaaaccatgcaaatgctgaatgag
ggcatcgttcccactgcgatgctggttgccaacgatcagatggcgctgggcgcaatgcgcgccattaccgagtcc
gggctgcgcgttggtgcggacatctcggtagtgggatacgacgataccgaagacagctcatgttatatcccgccg
ttaaccaccatcaaacaggattttcgcctgctggggcaaaccagcgtggaccgcttgctgcaactctctcaggcc
caggcggtgaagggcaatcagctgttgcccgtctcactggtgaaaagaaaaaccaccctggcgcccaatacgcaa
accgcctctccccgcgcgttggccgattcattaatgcagctggcacgacaggtttcccgactggaaagcgggcag
tgagcgcaacgcaattaatgtaagttagctcactcattaggcacgggatctcgaccgatgcccttgagagcctt
caacccagtcagctccttccggtgggcgcggggcatgactatcgtcgccgcacttatgactgtcttctttatcat
gcaactcgtaggacaggtgccggcagcgctctgggtcattttcggcgaggaccgctttcgctggagcgcgacgat
```

Figure 7 B gatcggcctgtcgcttgcggtattcggaatcttgcacgccctcgctcaagccttcgtcactggtcccgccaccaa
acgtttcggcgagaagcaggccattatcgccggcatggcggcccacgggtgcgcatgatcgtgctcctgtcgtt
gaggacccggctaggctggcggggttgccttactggttagcagaatgaatcaccgatacgcgagcgaacgtgaag
cgactgctgctgcaaaacgtctgcgacctgagcaacaacatgaatggtcttcggtttccgtgtttcgtaaagtct
ggaaacgcggaagtcagcgccctgcaccattatgttccggatctgcatcgcaggatgctgctggctaccctgtgg
aacacctacatctgtattaacgaagcgctggcattgaccctgagtgattttctctggtcccgccgcatccatac
cgccagttgtttaccctcacaacgttccagtaaccgggcatgttcatcatcagtaaccgtatcgtgagcatcct
ctctcgtttcatcggtatcattaccccatgaacagaaatcccccttacacggaggcatcagtgaccaaacagga
aaaaaccgcccttaacatggcccgctttatcagaagccagacattaacgcttctggagaaactcaacgagctgga
cgcggatgaacaggcagacatctgtgaatcgcttcacgaccacgctgatgagctttaccgcagctgcctcgcgcg
tttcggtgatgacggtgaaaacctctgacacatgcagctcccggagacggtcacagcttgtctgtaagcggatgc
cgggagcagacaagcccgtcagggcgcgtcagcgggtgttggcgggtgtcggggcgcagccatgacccagtcacg
tagcgatagcggagtgtatactggcttaactatgcggcatcagagcagattgtactgagagtgcaccatatatgc
ggtgtgaaataccgcacagatgcgtaaggagaaaataccgcatcaggcgctcttccgcttcctcgctcactgact
cgctgcgctcggtcgttcggctgcggcgagcggtatcagctcactcaaaggcggtaatacggttatccacagaat
caggggataacgcaggaaagaacatgtgagcaaaaggccagcaaaaggccaggaaccgtaaaaaggccgcgttgc
tggcgtttttccataggctccgcccccctgacgagcatcacaaaaatcgacgctcaagtcagaggtggcgaaacc
cgacaggactataaagataccaggcgtttccccctggaagctccctcgtgcgctctcctgttccgaccctgccgc
ttaccggatacctgtccgcctttctcccttcgggaagcgtggcgctttctcatagctcacgctgtaggtatctca
gttcggtgtaggtcgttcgctccaagctgggctgtgtgcacgaaccccccgttcagcccgaccgctgcgccttat
ccggtaactatcgtcttgagtccaacccggtaagacacgacttatcgccactggcagcagccactggtaacagga
ttagcagagcgaggtatgtaggcggtgctacagagttcttgaagtggtggcctaactacggctacactagaagga
cagtatttggtatctgcgctctgctgaagccagttaccttcggaaaaagagttggtagctcttgatccggcaaac
aaaccaccgctggtagcggtggtttttttgtttgcaagcagcagattacgcgcagaaaaaaaggatctcaagaag
atcctttgatcttttctacggggtctgacgctcagtggaacgaaaactcacgttaagggattttggtcatgagat
tatcaaaaaggatcttcacctagatccttttaaattaaaaatgaagttttaaatcaatctaaagtatatatgagt
aaacttggtctgacagttaccaatgcttaatcagtgaggcacctatctcagcgatctgtctatttcgttcatcca
tagttgcctgactccccgtcgtgtagataactacgatacgggagggcttaccatctggccccagtgctgcaatga
taccgcgagacccacgctcaccggctccagatttatcagcaataaaccagccagccggaagggccgagcgcagaa
gtggtcctgcaactttatccgcctccatccagtctattaattgttgccgggaagctagagtaagtagttcgccag
ttaatagtttgcgcaacgttgttgccattgctgcaggcatcgtggtgtcacgctcgtcgtttggtatggcttcat
tcagctccggttcccaacgatcaaggcgagttacatgatccccatgttgtgcaaaaaagcggttagctccttcg
gtcctccgatcgttgtcagaagtaagttggccgcagtgttatcactcatggttatggcagcactgcataattctc
ttactgtcatgccatccgtaagatgcttttctgtgactggtgagtactcaaccaagtcattctgagaatagtgta
tgcggcgaccgagttgctcttgcccggcgtcaatacgggataataccgcgccacatagcagaactttaaaagtgc

Figure 7 C

```
tcatcattggaaaacgttcttcggggcgaaaactctcaaggatcttaccgctgttgagatccagttcgatgtaac
ccactcgtgcacccaactgatcttcagcatcttttactttcaccagcgtttctgggtgagcaaaaacaggaaggc
aaaatgccgcaaaaagggaataaggcgacacggaaatgttgaatactcatactcttccttttcaatattatt
gaagcatttatcaggttattgtctcatgagcggatacatatttgaatgtatttagaaaaataaacaaatagggg
ttccgcgcacatttccccgaaaagtgccacctgaaattgtaaacgttaatattttgttaaaattcgcgttaaatt
tttgttaaatcagctcatttttaaccaataggccgaaatcggcaaaatcccttataaatcaaagaatagaccg
agatagggttgagtgttgttccagtttggaacaagagtccactattaaagaacgtggactccaacgtcaagggc
gaaaaaccgtctatcagggcgatggcccactacgtgaaccatcaccctaatcaagttttttggggtcgaggtgcc
gtaaagcactaaatcggaaccctaaagggagccccgatttagagcttgacggggaaagccggcgaacgtggcga
gaaaggaagggaagaaagcgaaaggagcgggcgctagggcgctggcaagtgtagcggtcacgctgcgcgtaacca
ccacaccgccgcgcttaatgcgccgctacagggcgcgtcccattcgcca
```

Figure 8

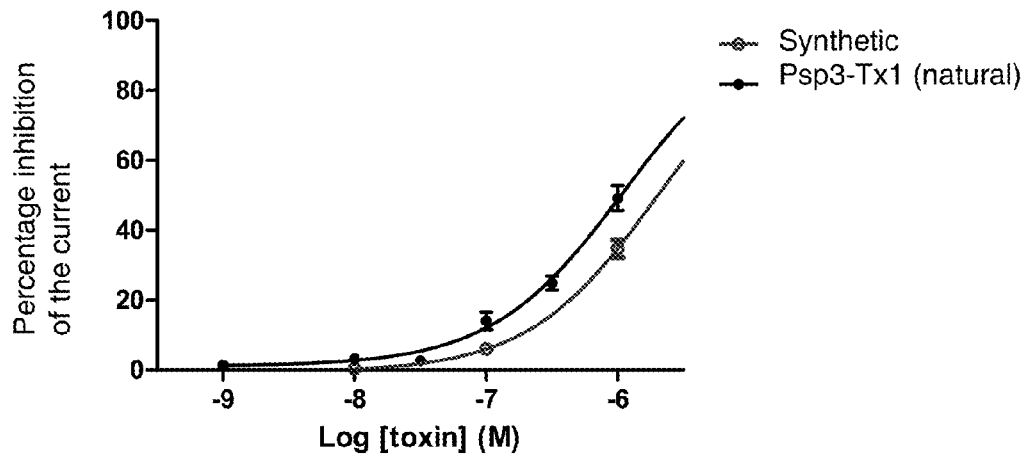

Inhibition of the recombinant Cav3.2
Synthetic peptide vs natural peptide

SEQUENCE LISTING

<160> NUMBER OF SEQ ID NOS: 6

<210> SEQ ID NO 1
<211> LENGTH: 28
<212> TYPE: PRT
<213> ORGANISM: Artificial Sequence
<220> FEATURE:
<223> OTHER INFORMATION: anagesic peptide

<400> SEQUENCE: 1

Tyr Cys Gln Lys Phe Leu Trp Thr Cys Asp Ser Glu Arg Pro Cys Cys
1               5                   10                  15

Glu Gly Leu Val Cys Arg Leu Trp Cys Lys Ile Asn
            20                  25

<210> SEQ ID NO 2
<211> LENGTH: 84
<212> TYPE: DNA
<213> ORGANISM: Artificial Sequence
<220> FEATURE:
<223> OTHER INFORMATION: nucleic acid sequence coding for the analgesic
      peptide

<400> SEQUENCE: 2
tattgccaga aatttctgtg gacctgcgat agcgaacgcc cgtgctgcga aggcctggtg     60
tgccgcctgt ggtgcaaaat taac                                           84

<210> SEQ ID NO 3

```
<211> LENGTH: 84
<212> TYPE: DNA
<213> ORGANISM: Artificial Sequence
<220> FEATURE:
<223> OTHER INFORMATION: sequence coding for an analgesic peptide
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (6)..(6)
<223> OTHER INFORMATION: y is c or t
<220> FEATURE:
<221> NAME/KEY: misc_feature
<222> LOCATION: (9)..(9)
<223> OTHER INFORMATION: r is a or g
<220> FEATURE:
<221> NAME/KEY: misc_feature
<222> LOCATION: (12)..(12)
<223> OTHER INFORMATION: r is a or g
<220> FEATURE:
<221> NAME/KEY: misc_feature
<222> LOCATION: (15)..(16)
<223> OTHER INFORMATION: y is c or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: y is c or t
<220> FEATURE:
<221> NAME/KEY: misc_feature
<222> LOCATION: (30)..(30)
<223> OTHER INFORMATION: y is c or t
<220> FEATURE:
<221> NAME/KEY: misc_feature
<222> LOCATION: (31)..(31)
<223> OTHER INFORMATION: w is a or t
<220> FEATURE:
<221> NAME/KEY: misc_feature
<222> LOCATION: (32)..(32)
<223> OTHER INFORMATION: s is c or g
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: r is a or g
<220> FEATURE:
<221> NAME/KEY: misc_feature
<222> LOCATION: (37)..(37)
<223> OTHER INFORMATION: m is a or c
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: y is c or t
<220> FEATURE:
<221> NAME/KEY: misc_feature
<222> LOCATION: (48)..(48)
<223> OTHER INFORMATION: y is c or t
<220> FEATURE:
<221> NAME/KEY: misc_feature
<222> LOCATION: (51)..(51)
```

```
<223> OTHER INFORMATION: r is a or g
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (55)..(55)
<223> OTHER INFORMATION: y is c or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: y is c or t
<220> FEATURE:
<221> NAME/KEY: misc_feature
<222> LOCATION: (64)..(64)
<223> OTHER INFORMATION: m is a or c
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (67)..(67)
<223> OTHER INFORMATION: y is c or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: y is c or t
<220> FEATURE:
<221> NAME/KEY: misc_feature
<222> LOCATION: (78)..(78)
<223> OTHER INFORMATION: r is a or g
<220> FEATURE:
<221> NAME/KEY: misc_feature
<222> LOCATION: (81)..(81)
<223> OTHER INFORMATION: h is a or c
<220> FEATURE:
<221> NAME/KEY: misc_feature
<222> LOCATION: (84)..(84)
<223> OTHER INFORMATION: y is c or t

<400> SEQUENCE: 3
taytgycara arttyytntg gacntgygay wsngarmgnc cntgytgyga rggnytngtn      60
tgymgnytnt ggtgyaarat haay                                            84

<210> SEQ ID NO 4
<211> LENGTH: 2481
<212> TYPE: DNA
<213> ORGANISM: Artificial Sequence
<220> FEATURE:
<223> OTHER INFORMATION: pT7-7 plasmid
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t

<400> SEQUENCE: 4
aattctcatg tttgacagct tatcatcgat aagcttgggc tgcaggtcga ctctagagga     60
```

```
tccccgggcg cgaattctag ccatatgtat atctccttct taaagttaaa caaaattatt    120
tctagaggga aaccgttgtg gtctccctat agtgagtcgt attaatttcg aagtctatca    180
gaagttcgaa tcgctgggcc tcgcgcgttt cggtgatgac ggtgaaaacc tctgacacat    240
gcagctcccg gagacggtca cagcttgtct gtaagcggat gccgggagca gacaagcccg    300
tcagggcgcg tcagcgggtg ttggcgggtg tcggggcgca gccatgaccc agtcacgtag    360
cgatagcgga gtgtatatac tggcttaact atgcggcatc agagcagatt gtactgagag    420
tgcaccanag atctntgcgg tgtgaaatac cgcacagatg cgtaaggaga aataccgca    480 tcaggcgctc ttccgcttcc tcgctcactg actcgctgcg ctcggtcgtt cggctgcggc    540
gagcggtatc agctcactca aaggcggtaa tacggttatc cacagaatca ggggataacg    600
caggaaagaa catgtgagca aaaggccagc aaaaggccag gaaccgtaaa aaggccgcgt    660
tgctggcgtt tttccatagg ctccgccccc ctgacgagca tcacaaaaat cgacgctcaa    720
gtcagaggtg gcgaaacccg acaggactat aaagatacca ggcgtttccc cctggaagct    780
ccctcgtgcg ctctcctgtt ccgaccctgc cgcttaccgg atacctgtcc gcctttctcc    840
cttcgggaag cgtggcgctt tctcaatgct cacgctgtag gtatctcagt tcggtgtagg    900
tcgttcgctc caagctgggc tgtgtgcacg aaccccccgt tcagcccgac cgctgcgcct    960
tatccggtaa ctatcgtctt gagtccaacc cggtaagaca cgacttatcg ccactggcag   1020
cagccactgg taacaggatt agcagagcga ggtatgtagg cggtgctaca gagttcttga   1080
agtggtggcc taactacggc tacactagaa ggacagtatt tggtatctgc gctctgctga   1140
agccagttac cttcggaaaa agagttggta gctcttgatc cggcaaacaa accaccgctg   1200
gtagcggtgg tttttttgtt tgcaagcagc agattacgcg cagaaaaaaa ggatctcaag   1260
aagatccttt gatcttttct acggggtctg acgctcagtg gaacgaaaac tcacgttaag   1320 ggatttggt catgagatta tcaaaaagga tcttcaccta gatccttta attcttgaag    1380 acgaaagggc ctcgtgatac gcctattttt ataggttaat gtcatgataa taatggtttc   1440
ttagacgtca ggtggcactt ttcggggaaa tgtgcgcgga acccctattt gtttattttt   1500
ctaaatacat tcaaatatgt atccgctcat gagacaataa ccctgataaa tgcttcaata   1560
atattgaaaa aggaagagta tgagtattca acatttccgt gtcgccctta ttcccttttt   1620
tgcggcattt tgccttcctg tttttgctca cccagaaacg ctggtgaaag taaaagatgc   1680
tgaagatcag ttgggtgcac gagtgggtta catcgaactg gatctcaaca gcggtaagat   1740
ccttgagagt tttcgccccg aagaacgttt tccaatgatg agcacttta aagttctgct    1800 atgtggcgcg gtattatccc gtgttgacgc cgggcaagag caactcggtc gccgcataca   1860
ctattctcag aatgacttgg ttgagtactc accagtcaca gaaaagcatc ttacggatgg   1920
catgacagta agagaattat gcagtgctgc cataaccatg agtgataaca ctgcggccaa   1980
cttacttctg acaacgatcg gaggaccgaa ggagctaacc gcttttttgc acaacatggg   2040
ggatcatgta actcgccttg atcgttggga accggagctg aatgaagcca taccaaacga   2100
cgagcgtgac accacgatgc ctgtagcaat ggcaacaacg ttgcgcaaac tattaactgg   2160
cgaactactt actctagctt cccggcaaca attaatagac tggatggagg cggataaagt   2220
tgcaggacca cttctgcgct cggcccttcc ggctggctgg tttattgctg ataaatctgg   2280
agccggtgag cgtgggtctc gcggtatcat tgcagcactg gggccagatg gtaagccctc   2340
ccgtatcgta gttatctaca cgacggggag tcaggcaact atggatgaac gaaatagaca   2400
gatcgctgag ataggtgcct cactgattaa gcattggtaa ctgtcagacc aagtttactc   2460
```

-continued atatatactt tagattgatt t                                               2481

<210> SEQ ID NO 5
<211> LENGTH: 4969
<212> TYPE: DNA
<213> ORGANISM: Artificial Sequence
<220> FEATURE:
<223> OTHER INFORMATION: pGex-4-T1 plasmid

<400> SEQUENCE: 5

```
acgttatcga ctgcacggtg caccaatgct tctggcgtca ggcagccatc ggaagctgtg     60
gtatggctgt gcaggtcgta atcactgca taattcgtgt cgctcaaggc gcactcccgt    120
tctggataat gttttttgcg ccgacatcat aacggttctg gcaaatattc tgaaatgagc    180
tgttgacaat taatcatcgg ctcgtataat gtgtggaatt gtgagcggat aacaatttca    240
cacaggaaac agtattcatg tccctataac taggttattg gaaaattaag ggccttgtgc    300
aacccactcg acttcttttg aatatcttg aagaaaaata tgaagagcat ttgtatgagc    360
gcgatgaagg tgataaatgg cgaaacaaaa agtttgaatt gggtttggag tttcccaatc    420
ttccttatta tattgatggt gatgttaaat taacacagtc tatggccatc atacgttata    480
tagctgacaa gcacaacatg ttgggtggtt gtccaaaaga gcgtgcagag atttcaatgc    540
ttgaaggagc ggttttggat attagatacg gtgtttcgag aattgcatat agtaaagact    600
ttgaaactct caaagttgat tttcttagca agctacctga atgctgaaa atgttcgaag    660
atcgtttatg tcataaaaca tatttaaatg gtgatcatgt aacccatcct gacttcatgt    720
tgtatgacgc tcttgatgtt gttttataca tggacccaat gtgcctggat gcgttcccaa    780
aattagtttg ttttaaaaaa cgtattgaag ctatcccaca aattgataag tacttgaaat    840
ccagcaagta tatagcatgg ccttttgcagg gctggcaagc cacgtttggt ggtggcgacc    900
atcctccaaa atcggatctg ttccgcgtg atccccgga attcccgggt cgactcgagc    960
ggccgcatcg tgactgactg acgatctgcc tcgcgcgttt cggtgatgac ggtgaaaacc   1020
tctgacacat gcagctcccg agacggtca cagcttgtct gtaagcggat gccgggagca   1080
gacaagcccg tcagggcgcg tcagcgggtg ttggcgggtg tcggggcgca gccatgaccc   1140
agtcacgtag cgatagcgga gtgtataatt cttgaagacg aaagggcctc gtgatacgcc   1200
tatttttata ggttaatgtc atgataataa tggtttctta cgtcaggt ggcacttttc    1260
ggggaaatgt gcgcggaacc cctatttgtt tatttttcta atacattca aatatgtatc   1320
cgctcatgag acaataaccc tgataaatgc ttcaataata ttgaaaaagg aagagtatga   1380
gtattcaaca tttccgtgtc gcccttattc ccttttttgc ggcattttgc cttcctgttt   1440
ttgctcaccc agaaacgctg gtgaaagtaa aagatgctga agatcagttg ggtgcacgag   1500
tgggttacat cgaactggat ctcaacagcg gtaagatcct tgagagtttt cgccccgaag   1560
aacgttttcc aatgatgagc acttttaaag ttctgctatg tggcgcggta ttatcccgtg   1620
ttgacgccgg gcaagagcaa ctcggtcgcc gcatacacta ttctcagaat gacttggttg   1680
agtactcacc agtcacagaa aagcatctta cggatggcat gacagtaaga gaattatgca   1740
gtgctgccat aaccatgagt gataacactg cggccaactt acttctgaca acgatcggag   1800
gaccgaagga gctaaccgct ttttgcaca catgggggga tcatgtaact cgccttgatc   1860
gttgggaacc ggagctgaat gaagccatac caaacgacga gcgtgacacc acgatgcctg   1920
cagcaatggc aacaacgttg cgcaaactat taactggcga actacttact ctagcttccc   1980
ggcaacaatt aatagactgg atggaggcgg ataaagttgc aggaccactt ctgcgctcgg   2040
```

```
cccttccggc tggctggttt attgctgata atctggagc cggtgagcgt gggtctcgcg   2100
gtatcattgc agcactgggg ccagatggta agccctcccg tatcgtagtt atctacacga   2160
cggggagtca ggcaactatg gatgaacgaa atagacagat cgctgagata ggtgcctcac   2220
tgattaagca ttggtaactg tcagaccaag tttactcata tactttag attgatttaa     2280 aacttcattt ttaatttaaa aggatctagg tgaagatcct ttttgataat ctcatgacca   2340
aaatccctta acgtgagttt tcgttccact gagcgtcaga ccccgtagaa aagatcaaag   2400
gatcttcttg agatcctttt tttctgcgcg taatctgctg cttgcaaaca aaaaaaccac   2460
cgctaccagc ggtggtttgt ttgccggatc aagagctacc aactctttt ccgaaggtaa    2520 ctggcttcag cagagcgcag ataccaaata ctgtccttct agtgtagccg tagttaggcc   2580
accacttcaa gaactctgta gcaccgccta catacctcgc tctgctaatc ctgttaccag   2640
tggctgctgc cagtggcgat aagtcgtgtc ttaccgggtt ggactcaaga cgatagttac   2700
cggataaggc gcagcggtcg ggctgaacgg ggggttcgtg cacacagccc agcttggagc   2760
gaacgaccta caccgaactg agatacctac agcgtgagct atgagaaagc gccacgcttc   2820
ccgaagggag aaaggcggac aggtatccgg taagcggcag ggtcggaaca ggagagcgca   2880
cgagggagct ccaggggga acgcctggt atctttatag tcctgtcggg tttcgccacc      2940
tctgacttga gcgtcgattt ttgtgatgct cgtcaggggg gcggagccta tggaaaaacg   3000
ccagcaacgc ggccttttta cggttcctgg ccttttgctg gccttttgct cacatgttct   3060
ttcctgcgtt atccctgat tctgtggata accgtattac cgcctttgag tgagctgata    3120
ccgctcgccg cagccgaacg accgagcgca gcgagtcagt gagcgaggaa gcggaagagc   3180
gcctgatgcg gtattttctc cttacgcatc tgtgcggtat ttcacaccgc ataaattccg   3240
acaccatcga atggtgcaaa acctttcgcg gtatggcatg atagcgcccg gaagagagtc   3300
aattcagggt ggtgaatgtg aaaccagtaa cgttatacga tgtcgcagag tatgccggtg   3360
tctcttatca gaccgtttcc cgcgtggtga accaggccag ccacgtttct gcgaaaacgc   3420
gggaaaaagt ggaagcggcg atggcggagc tgaattacat tcccaaccgc gtggcacaac   3480
aactggcggg caaacagtcg ttgctgattg gcgttgccac ctccagtctg gccctgcacg   3540
cgccgtcgca aattgtcgcg gcgattaaat ctcgcgccga tcaactgggt gccagcgtgg   3600
tggtgtcgat ggtagaacga agcggcgtcg aagcctgtaa agcggcggtg cacaatcttc   3660
tcgcgcaacg cgtcagtggg ctgatcatta actatccgct ggatgaccag gatgccattg   3720
ctgtggaagc tgcctgcact aatgttccgg cgttatttct tgatgtctct gaccagacac   3780
ccatcaacag tattattttc tcccatgaag acggtacgcg actgggcgtg gagcatctgg   3840
tcgcattggg tcaccagcaa atcgcgctgt tagcgggccc attaagttct gtctcggcgc   3900
gtctgcgtct ggctggctgg cataaatatc tcactcgcaa tcaaattcag ccgatagcgg   3960
aacgggaagg cgactggagt gccatgtccg gttttcaaca aaccatgcaa atgctgaatg   4020
agggcatcgt tcccactgcg atgctggttg ccaacgatca gatggcgctg ggcgcaatgc   4080
gcgccattac cgagtccggg ctgcgcgttg gtgcggatat ctcggtagtg ggatacgacg   4140
ataccgaaga cagctcatgt tatatcccgc cgttaaccac catcaaacag gattttcgcc   4200
tgctggggca aaccagcgtg gaccgcttgc tgcaactctc tcaggccag gcggtgaagg     4260 gcaatcagct gttgcccgtc tcactggtga aaagaaaaac caccctggcg cccaatacgc   4320
aaaccgcctc tccccgcgcg ttggccgatt cattaatgca gctggcacga caggtttccc   4380
gactggaaag cgggcagtga gcgcaacgca attaatgtga gttagctcac tcattaggca   4440
```

-continued

```
ccccaggctt tacactttat gcttccggct cgtatgttgt gtggaattgt gagcggataa    4500
caatttcaca caggaaacag ctatgaccat gattacggat tcactggccg tcgttttaca    4560
acgtcgtgac tgggaaaacc ctggcgttac ccaacttaat cgccttgcag cacatccccc    4620
tttcgccagc tggcgtaata gcgaagaggc ccgcaccgat cgcccttccc aacagttgcg    4680
cagcctgaat ggcgaatggc gctttgcctg gtttccggca ccagaagcgg tgccggaaag    4740
ctggctggag tgcgatcttc ctgaggccga tactgtcgtc gtcccctcaa actggcagat    4800
gcacggttac gatgcgccca tctacaccaa cgtaacctat cccattacgg tcaatccgcc    4860
gtttgttccc acgagaatc cgacgggttg ttactcgctc acatttaatg ttgatgaaag    4920
ctggctacag gaaggccaga cgcgaattat ttttgatggc gttggaatt              4969
```

<210> SEQ ID NO 6
<211> LENGTH: 5900
<212> TYPE: DNA
<213> ORGANISM: Artificial Sequence
<220> FEATURE:
<223> OTHER INFORMATION: pET32 plasmid

<400> SEQUENCE: 6

```
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacggagct cgaattcgga tccgatatca gccatggcct gtcgtcgtc gtcggtaccc    240
agatctgggc tgtccatgtg ctggcgttcg aatttagcag cagcggtttc tttcatacca    300
gaaccgcgtg gcaccagacc agaagaatga tgatgatgat ggtgcatatg ccagaaccca    360
gaaccggcca ggttagcgtc gaggaactct ttcaactgac ctttagacag tgcacccact    420
ttggttgccg ccacttcacc gttttttgaac agcagcagag tcgggatacc acggatgcca    480
tatttcggcg cagtgccagg gttttgatcg atgttcagtt ttgcaacggt cagtttgccc    540
tgatattcgt cagcgatttc atccagaatc ggggcgatca ttttgcacgg accgcaccac    600
tctgcccaga aatcgacgag gatcgccccg tccgctttga gtacatccgt gtcaaaactg    660
tcgtcagtca ggtgaataat tttatcgctc atatgtatat ctccttctta aagttaaaca    720
aaattatttc tagaggggaa ttgttatccg ctcacaattc ccctatagtg agtcgtatta    780
atttcgcggg atcgagatcg atctcgatcc tctacgccgg acgcatcgtg gccggcatca    840
ccggcgccac aggtgcggtt gctggcgcct atatcgccga catcaccgat ggggaagatc    900
gggctcgcca cttcgggctc atgagcgctt gtttcggcgt gggtatggtg gcaggccccg    960
tggcggggg actgttgggc gccatctcct tgcatgcacc attccttgcg gcggcggtgc   1020
tcaacggcct caacctacta ctgggctgct tcctaatgca ggagtcgcat aagggagagc   1080
gtcgagatcc cggacaccat cgaatggcgc aaaacctttc gcggtatggc atgatagcgc   1140
ccggaagaga gtcaattcag gtggtgaat gtgaaaccag taacgttata cgatgtcgca   1200
gagtatgccg gtgtctctta tcagaccgtt tcccgcgtgg tgaaccaggc cagccacgtt   1260
tctgcgaaaa cgcgggaaaa agtggaagcg gcgatggcgg agctgaatta cattcccaac   1320
cgcgtggcac aacaactggc gggcaaacag tcgttgctga ttggcgttgc cacctccagt   1380
ctggccctgc acgcgccgtc gcaaattgtc gcggcgatta atctcgcgc cgatcaactg   1440
ggtgccagcg tggtggtgtc gatggtagaa cgaagcggcg tcgaagcctg taaagcggcg   1500
gtgcacaatc ttctcgcgca acgcgtcagt gggctgatca ttaactatcc gctggatgac   1560
```

```
caggatgcca ttgctgtgga agctgcctgc actaatgttc cggcgttatt tcttgatgtc    1620
tctgaccaga cacccatcaa cagtattatt ttctcccatg aagacggtac gcgactgggc    1680
gtggagcatc tggtcgcatt gggtcaccag caaatcgcgc tgttagcggg cccattaagt    1740
tctgtctcgg cgcgtctgcg tctggctggc tggcataaat atctcactcg caatcaaatt    1800
cagccgatag cggaacggga aggcgactgg agtgccatgt ccggttttca acaaaccatg    1860
caaatgctga atgagggcat cgttcccact gcgatgctgg ttgccaacga tcagatggcg    1920
ctgggcgcaa tgcgcgccat taccgagtcc gggctgcgcg ttggtgcgga catctcggta    1980
gtgggatacg acgataccga agacagctca tgttatatcc cgccgttaac caccatcaaa    2040
caggattttc gcctgctggg gcaaaccagc gtggaccgct tgctgcaact ctctcagggc    2100
caggcggtga agggcaatca gctgttgccc gtctcactgg tgaaaagaaa aaccaccctg    2160
gcgcccaata cgcaaaccgc ctctccccgc gcgttggccg attcattaat gcagctggca    2220
cgacaggttt cccgactgga aagcgggcag tgagcgcaac gcaattaatg taagttagct    2280
cactcattag gcaccgggat ctcgaccgat gcccttgaga gccttcaacc cagtcagctc    2340
cttccggtgg gcgcggggca tgactatcgt cgccgcactt atgactgtct tctttatcat    2400
gcaactcgta ggacaggtgc cggcagcgct ctgggtcatt ttcggcgagg accgctttcg    2460
ctggagcgcg acgatgatcg gcctgtcgct tgcggtattc ggaatcttgc acgccctcgc    2520
tcaagccttc gtcactggtc cgccaccaa acgtttcggc gagaagcagg ccattatcgc    2580
cggcatggcg gccccacggg tgcgcatgat cgtgctcctg tcgttgagga cccggctagg    2640 ctggcgggt tgccttactg gttagcagaa tgaatcaccg atacgcgagc gaacgtgaag    2700
cgactgctgc tgcaaaacgt ctgcgacctg agcaacaaca tgaatggtct tcggtttccg    2760
tgtttcgtaa agtctggaaa cgcggaagtc agcgccctgc accattatgt tccggatctg    2820
catcgcagga tgctgctggc taccctgtgg aacacctaca tctgtattaa cgaagcgctg    2880
gcattgaccc tgagtgattt ttctctggtc ccgccgcatc cataccgcca gttgtttacc    2940
ctcacaacgt tccagtaacc gggcatgttc atcatcagta acccgtatcg tgagcatcct    3000
ctctcgtttc atcggtatca ttaccccccat gaacagaaat ccccccttaca cggaggcatc    3060 agtgaccaaa caggaaaaaa ccgcccttaa catggcccgc tttatcagaa gccagacatt    3120
aacgcttctg gagaaactca acgagctgga cgcggatgaa caggcagaca tctgtgaatc    3180
gcttcacgac cacgctgatg agctttaccg cagctgcctc gcgcgtttcg gtgatgacgg    3240
tgaaaacctc tgacacatgc agctcccgga gacggtcaca gcttgtctgt aagcggatgc    3300
cgggagcaga caagcccgtc agggcgcgtc agcgggtgtt ggcgggtgtc ggggcgcagc    3360
catgacccag tcacgtagcg atagcggagt gtatactggc ttaactatgc ggcatcagag    3420
cagattgtac tgagagtgca ccatatatgc ggtgtgaaat accgcacaga tgcgtaagga    3480
gaaaataccg catcaggcgc tcttccgctt cctcgctcac tgactcgctg cgctcggtcg    3540
ttcggctgcg gcgagcggta tcagctcact caaaggcggt aatacggtta tccacagaat    3600
caggggataa cgcaggaaag aacatgtgag caaaaggcca gcaaaaggcc aggaaccgta    3660
aaaaggccgc gttgctggcg tttttccata ggctccgccc ccctgacgag catcacaaaa    3720
atcgacgctc aagtcagagg tggcgaaacc cgacaggact ataaagatac caggcgtttc    3780 ccccctggaag ctccctcgtg cgctctcctg ttccgaccct gccgcttacc ggatacctgt    3840
ccgcctttct cccttcggga agcgtggcgc tttctcatag ctcacgctgt aggtatctca    3900
gttcggtgta ggtcgttcgc tccaagctgg gctgtgtgca cgaaccccc gttcagcccg    3960
```

```
accgctgcgc cttatccggt aactatcgtc ttgagtccaa cccggtaaga cacgacttat   4020
cgccactggc agcagccact ggtaacagga ttagcagagc gaggtatgta ggcggtgcta   4080
cagagttctt gaagtggtgg cctaactacg gctacactag aaggacagta tttggtatct   4140
gcgctctgct gaagccagtt accttcggaa aaagagttgg tagctcttga tccggcaaac   4200
aaaccaccgc tggtagcggt ggttttttg tttgcaagca gcagattacg cgcagaaaaa   4260
aaggatctca agaagatcct ttgatctttt ctacggggtc tgacgctcag tggaacgaaa   4320
actcacgtta agggattttg gtcatgagat tatcaaaaag gatcttcacc tagatccttt   4380
taaattaaaa atgaagtttt aaatcaatct aaagtatata tgagtaaact tggtctgaca   4440
gttaccaatg cttaatcagt gaggcaccta tctcagcgat ctgtctattt cgttcatcca   4500
tagttgcctg actccccgtc gtgtagataa ctacgatacg ggagggctta ccatctggcc   4560
ccagtgctgc aatgataccg cgagacccac gctcaccggc tccagattta tcagcaataa   4620
accagccagc cggaagggcc gagcgcagaa gtggtcctgc aactttatcc gcctccatcc   4680
agtctattaa ttgttgccgg gaagctagag taagtagttc gccagttaat agtttgcgca   4740
acgttgttgc cattgctgca ggcatcgtgg tgtcacgctc gtcgtttggt atggcttcat   4800
tcagctccgg ttcccaacga tcaaggcgag ttacatgatc ccccatgttg tgcaaaaaag   4860
cggttagctc cttcggtcct ccgatcgttg tcagaagtaa gttggccgca gtgttatcac   4920
tcatggttat ggcagcactg cataattctc ttactgtcat gccatccgta agatgctttt   4980
ctgtgactgg tgagtactca accaagtcat tctgagaata gtgtatgcgg cgaccgagtt   5040
gctcttgccc ggcgtcaata cgggataata ccgcgccaca tagcagaact ttaaaagtgc   5100
tcatcattgg aaaacgttct cggggcgaaa actctcaag gatcttaccg ctgttgagat   5160
ccagttcgat gtaacccact cgtgcaccca actgatcttc agcatctttt actttcacca   5220
gcgtttctgg gtgagcaaaa acaggaaggc aaaatgccgc aaaaaaggga ataagggcga   5280
cacggaaatg ttgaatactc atactcttcc tttttcaata ttattgaagc atttatcagg   5340
gttattgtct catgagcgga tacatatttg aatgtattta gaaaaataaa caaataggg   5400
ttccgcgcac atttccccga aaagtgccac ctgaaattgt aaacgttaat attttgttaa   5460
aattcgcgtt aaattttgt taaatcagct cattttttaa ccaataggcc gaaatcggca   5520
aaatccctta taaatcaaaa gaatagaccg agatagggtt gagtgttgtt ccagtttgga   5580
acaagagtcc actattaaag aacgtggact ccaacgtcaa agggcgaaaa accgtctatc   5640
agggcgatgg cccactacgt gaaccatcac cctaatcaag ttttttgggg tcgaggtgcc   5700
gtaaagcact aaatcggaac cctaaaggga ccccgatt tagagcttga cggggaaagc   5760
cggcgaacgt ggcgagaaag gaagggaaga aagcgaaagg agcgggcgct agggcgctgg   5820
caagtgtagc ggtcacgctg cgcgtaacca ccacacccgc cgcgcttaat gcgccgctac   5880
agggcgcgtc ccattcgcca                                              5900
```

IDENTIFICATION OF NOVEL ANTAGONIST TOXINS OF T-TYPE CALCIUM CHANNEL FOR ANALGESIC PURPOSES

TECHNICAL FIELD OF THE INVENTION

The present invention relates to a toxin that is a T-type calcium channel antagonist. In particular, it relates to a peptide making up a peptide, to the nucleic acids coding for said peptide, and to the use of said peptide as antagonist and/or inverse agonist of T-type calcium channels. The present invention also relates to the use of this peptide for manufacturing a medicinal product.

It finds application notably in the treatment of pain, in cardiovascular disorders, in the treatment of erectile dysfunction and potentially in the treatment of cancers.

In the following description, the references indicated with "Ref." refer to the list of references given after the examples.

PRIOR ART

The management and treatment of pain are essential for quality of life. Pain affects a large number of people. It is estimated that, in Europe, 60 million people are affected by pain each year, which represents an annual cost of 1 billion dollars in medicines for its treatment. The annual expenditure on analgesic drugs can be evaluated at about 25 billion dollars and is expected to reach 42 billion in 2010. Pain is divided into two categories: acute pain and chronic pain. Acute pain corresponds to rapid, brief pain, of limited duration, as opposed to chronic pain, which is persistent pain, which may be associated, for example, with hyperalgesia.

Numerous studies have been carried out for identifying the mechanisms by which pain is transmitted. Transmission of the pain signal by the nervous system involves neuronal receptors, which convert the painful stimulus into an electrical signal. The latter will then be transmitted to the central nervous system by the nerves, involving specific molecular receptors.

Among the various sensory neurons, we may mention the nociceptive neurons, which react specifically to painful stimuli.

Owing to their specificity, the nociceptive neurons possess a unique repertory of ion channels, which are proteins responsible for the cellular excitability and which represent a major class of drug targets. Thus, the ion channels specifically expressed in the nociceptive neurons represent as many targets for the discovery of new analgesics.

Molecules that inhibit pain, or analgesics, have been known for a very long time. We may mention for example the class of opiates, which act upon the signaling of the painful signal and stimulate the nerve pathways that inhibit pain. Other molecules are used for treating chronic pain. These are for example molecules acting on the GABA receptors such as badofene, diazepan, tizanidine and dartrolene.

The analgesic substances currently used have several drawbacks. It is well known that the opioid derivatives can cause hallucinatory phenomena and cardiorespiratory depression. They are also a source of dependency, for example dependency on morphine, methadone etc. Finally, treatment with opiates is associated with undesirable effects such as severe constipation.

There are also cases of development of tolerance to these medicinal products, i.e. the dose required to obtain a constant effect must be increased. This tolerance increases over time and therefore leads to it being necessary to increase the doses and may lead to the drug becoming ineffective. In fact, the required amount can become greater than the toxic dose of said drug.

For example, in the case of neuropathic pain, which may develop in diabetes, cancer, chemotherapy treatments, chronic inflammatory pains, in cases of irritable bowel syndrome etc., treatment of pain with known analgesics often induces a phenomenon of tolerance and therefore problems in the treatment of said pain.

There is therefore a real need to find novel analgesic substances to alleviate these faults, drawbacks and obstacles of the prior art in order to reduce the costs and improve the treatment of pain and patients' comfort.

SUMMARY OF THE INVENTION

The inventors showed in experiments of inhibition of expression of the Cacna1h gene coding for the T-type calcium channel $Ca_V3.2$ present in nociceptors that said channel is involved in pain perception.

The Cav3.2 channels form part of the family of "low-threshold" or "T-type" calcium channels and are expressed in nociceptive neurons.

By using an approach of gene repression by intrathecal injection of antisense DNA in the rat as described in Bourinet, E., et al., "Silencing of the CaV3.2 T-type calcium channel gene in sensory neurons demonstrates its major role in nociception". Embo J, 2005. 24 (2): p. 315-24 (Ref 1), the inventors demonstrated that depletion of the $Ca_V3.2$ calcium channels in the nociceptive neurons of healthy animals or in a condition of neuropathy leads to highly effective analgesia. Accordingly, the T-type calcium channels represent a potential target for the development of new therapeutic approaches to the treatment of pain.

Moreover, it has been demonstrated that the $Ca_V3.2$ calcium channels are involved in cellular proliferation (Taylor, J. T., Zeng, X. B., Pottle, J. E., Lee, K., Wang, A. R., Yi, S. G., Scruggs, J. A., Sikka, S. S. and Li, M. (2008) Calcium signaling and T-type calcium channels in cancer cell cycling. *World J Gastroenterol*, 14, 4984-4991 (Ref 8)) and in the regulation of blood pressure (Chen, C. C., Lamping, K. G., Nuno, D. W., Barresi, R., Prouty, S. J., Lavoie, J. L., Cribbs, L. L., England, S. K., Sigmund, C. D., Weiss, R. M., Williamson, R. A., Hill, J. A. and Campbell, K. P. (2003) Abnormal coronary function in mice deficient in alpha1H T-type Ca2+ channels. *Science*, 302, 1416-1418. (Ref 9)). The T-type calcium channels represent a potential target for development of new therapeutic approaches to the treatment of hypertension and of cancers, for example cancers associated with uncontrolled proliferation of cancer cells.

It can be cancers of various organs, for example:

prostate cancer (see Gackiere F, Bidaux G, Delcourt P, Van Coppenolle F, Katsogiannou M, Dewailly E, Bavencoffe A, Van Chuoï-Mariot M T, Mauroy B, Prevarskaya N, Mariot P. (2008) CaV3.2 T-type calcium channels are involved in calcium-dependent secretion of neuroendocrine prostate cancer cells. J Biol Chem, 283 (15):10162-73 (Ref 16), glioma (see Panner A, Cribbs L L, Zainelli G M, Origitano T C, Singh S, Wurster R D. (2005) Variation of T-type calcium channel protein expression affects cell division of cultured tumor cells. Cell Calcium, 37 (2):105-19 (Ref 11)), esophageal carcinoma (see Lu F, Chen H, Zhou C, Liu S, Guo M, Chen P, Zhuang H, Xie D, Wu S. (2008) T-type Ca2+ channel expression in human esophageal carcinomas: a functional role in proliferation Cell Calcium. 43 (1):49-58 (Ref 12))

breast cancer (see Taylor J T, Huang L, Pottle J E, Liu K, Yang Y, Zeng X, Keyser B M, Agrawal K C, Hansen J B, Li M (2008) Selective blockade of T-type Ca2+ channels suppresses human breast cancer cell proliferation. Cancer Lett, 18; 267 (1):116-24 (Ref 13).

In particular, a pharmacological approach using selective antagonists of the Cav3.2 T-type channel is the object of the present patent.

Thus, the invention meets the need to find new analgesic substances, by providing a novel molecule that is notably capable of inhibiting a painful signal, more particularly a molecule that is capable of inhibiting the receptors responsible for this signal. This molecule is a peptide of sequence: YCQKFLWTCDSERPCCEGLVCRLWCKIN (SEQ ID NO 1) or a derivative thereof.

"Derivative" means that these "fragments" or "derivatives" are such that they conserve the properties of the peptide of the present invention. The derivatives or fragment can also be considered to be analogs of the peptide of the present invention.

For example, a derivative can be the peptide of sequence ID NO1 with modifications on at least one of the amino acids. The modifications are for example as follows:
  replacement of at least one amino acid with another of the same family (aromatic, hydrophobic, basic, etc.);
  replacement of a natural amino acid (L amino acid) with the same amino acid in the D form;
  replacement of a peptide bond between two amino acids with a pseudopeptide bond.
  modification independently of the N- and C-terminal ends of the peptide.

It will be possible for these derivatives to comprise natural amino acids, modified amino acids, for example selenocysteines, non-natural amino acids, and/or structural modifications of the peptide such as cyclizations.

The derivatives can, for example, also comprise peptides modified for the purpose of labeling with agents such as biotin, fluorophore groups or a radioactive isotope.

The modifications of the N- or C-terminal ends can be for example isoprenylation, glypiation, myristoylation, or palmitoylation. The C-terminal end can also be modified for example by amidation leading to the formation of an amide function at the C-terminal end. Examples of post-translational modifications occurring in peptides are presented in Han K K, Martinage A (1992) Post-translational chemical modification(s) of proteins. Int J Biochem. 24 (1):19-28.; Walsh G, Jefferis R (2006) Post-translational modifications in context of therapeutic proteins *Nature Biotechnology*—24, 1241-1252 (Ref 17)). These modifications are modifications that may be encountered in insect venoms (see for example Escoubas P. (2006) Molecular diversification in spider venoms: a web of combinatorial peptide libraries. Mol Divers. 10 (4):545-54 (Ref 18)).

In the description given hereunder, peptide of sequence ID NO 1 means the peptide sequence ID NO 1 or a sequence derived therefrom.

The invention also meets the need to find new antihypertensive molecules by providing a novel molecule that is notably capable of lowering blood pressure.

The invention also meets the need to find new molecules for cancer treatment by providing a novel molecule that is notably capable of inhibiting cellular proliferation.

The novel molecule of the present invention is a peptide. This peptide was isolated for the first time by the inventors from the venom of a spider of the genus *Paraphysa* (Psp3) (Araneae: Theraphosidae).

Moreover, the present invention also relates to any nucleic acid sequence coding for the peptide of sequence YCQKFLWTCDSERPCCEGLVCRLWCKIN (SEQ ID NO 1).

The nucleic acid of the present invention can be any sequence coding for the peptide of sequence SEQ ID NO 1 taking into account the degeneration of the genetic code. For example, it can be nucleic acids of the following sequences:

```
                                              (SEQ ID NO 2)
5' TAT TGC CAG AAA TTT CTG TGG ACC TGC GAT AGC

GAA CGC CCG TGC TGC GAA GGC CTG GTG TGC CGC CTG

TGG TGC AAA ATT AAC 3'

(SEQ ID NO 3)
5' TAY TGY CAR AAR TTY YTN TGG ACN TGY GAY WSN

GAR MGN CCN TGY TGY GAR GGN YTN GTN TGY MGN YTN

TGG TGY AAR ATH AAY 3'
``` in which A is adenosine, C is cytidine, G is guanosine, T is thymidine and H is A or C or T, M is A or C, N is A or C or G or T, R is A or G, S is C or G, W is A or T and Y is C or T:

The invention also relates to an expression system comprising a plasmid and/or an expression vector coding for the peptide SEQ ID NO 1.

In the present invention, the expression system can comprise at least one nucleic acid sequence coding for the peptide of sequence YCQKFLWTCDSERPCCEGLVCRLWCKIN (SEQ ID NO 1).

"Expression vector" means, in the present invention, a nucleic acid sequence into which it is possible to insert one or more fragments of nucleic acids that we wish to express in a host. The expression vector can comprise the elements permitting expression of the nucleic acid sequence in the host. For example, the vector can comprise a promoter sequence, a sequence coding for a peptide signal. The vectors can be any vector known by a person skilled in the art.

For example, the expression vectors can be selected from the group comprising plasmids, viruses, bacterial vectors, yeast artificial chromosomes (YAC) and bacterial artificial chromosomes (BAC). The expression vectors can also be vectors of overexpression of recombinant proteins, with or without fusion to a soluble protein such as, for example, GST, or thioredoxin or any other fusion protein known by a person skilled in the art.

For example, vectors usable in the present invention can notably be selected from the group comprising the plasmid pT7-7 (SEQ ID NO 4, FIG. 5), a plasmid of the pGEX series (SEQ ID NO 5, FIG. 6), marketed for example by the company Pharmacia, or a plasmid of the pET32 series (SEQ ID NO 6, FIG. 7), marketed for example by the company Novagen.

The invention also relates to a host comprising an expression vector of the peptide of sequence YCQKFLWTCDSERPCCEGLVCRLWCKIN (SEQ ID NO1).

In the present invention, "host" means any cell that can be transformed with an expression vector or modified genetically in order to produce the peptide of the invention.

The transformation of said "host" can be performed for example by electroporation or by any other method known by a person skilled in the art. The sequence coding for the peptide of sequence ID NO 1 used during transformation can be free or incorporated in one of the aforementioned vectors. After introduction, said nucleic acid sequence can be incorporated into the genome of the host by genetic recombination, remain in the free form in the host and/or remain in the vector, said nucleic acid sequence then being recognized by the proteins and/or enzymes of the host and expressed thereby.

The host can be selected from the group comprising eukaryotic or prokaryotic cells, for example bacteria such as *Escherichia coli*, yeasts such as *Pichia pastoris*, insect cells such as cells of *Drosophila* or of *Spodoptera*, mammalian cells and any other cell known by a person skilled in the art that enables peptides and/or proteins to be produced from expression vectors.

The prokaryotic or eukaryotic cells can, preferably, permit overexpression of the peptide encoded by the vector. Thus, any host cell capable of expressing an expression vector for the peptide of the invention can be used, for example *Escherichia coli*.

Preferably, the eukaryotic or prokaryotic cells selected are those that permit overexpression of the peptide of the invention. For example, they are Sf9 cells of *Spodoptera*, S2 cells of *Drosophila*, yeasts of the *Pichia pastoris* type or *Escherichia coli* bacteria.

The inventors show in the examples given below that the peptide of sequence SEQ ID NO 1 is an antagonist and/or a partial antagonist of T-type channels.

Moreover, the present invention also relates to the use of the peptide of sequence YCQKFLWTCDSERPCCEGLVCRLWCKIN (SEQ ID NO 1) as antagonist of a T-type calcium channel.

"Antagonist" means an agent, for example a chemical molecule, a protein, a peptide etc. that interacts with a receptor site on the channel and that prevents said channel from functioning.

The antagonist can also decrease the pharmacological effect of the agonist, and then it is a "partial antagonist".

The invention also relates to the use of the peptide of sequence SEQ ID NO 1 as inverse agonist of a T-type channel. "Inverse agonist" means an agent, for example a chemical molecule, a protein etc., which interacts with the same receptor as an agonist of this receptor but produces the opposite pharmacological effect.

In other words, the antagonist, partial antagonist or inverse agonist can be a substance that attaches to the same cellular receptors at identical or different sites of a reference substance, preventing the latter producing all or part of its usual effects or producing the opposite effect.

In the present invention, "T-type calcium channels" means calcium channels with a low activation threshold, i.e. having an activation potential between −80 and −20 mV, preferably between −70 and −50 mV.

For example, T-type calcium channels can be calcium channels generated by the subunits $Ca_V3.1$, $Ca_V3.2$, $Ca_V3.3$ and all their splicing variants whether or not in combination with their regulatory subunits.

Preferably, the peptide is used as antagonist and/or inverse agonist of the T-type calcium channels.

Even more preferably, the peptide is used as antagonist and/or inverse agonist of the $Ca_V3.2$ calcium channels and/or of the $Ca_V3.1$ and/or $Ca_V3.3$ calcium channels.

The invention also relates to the use of the peptide of sequence YCQKFLWTCDSERPCCEGLVCRLWCKIN (SEQ ID NO 1) and/or of a nucleic acid coding for the peptide of sequence YCQKFLWTCDSERPCCEGLVCRLWCKIN (SEQ ID NO 1) for manufacturing a drug. This drug can be for human or veterinary use.

In the present invention, the peptide can be combined with any pharmacologically acceptable carrier, in order for example to improve its bioavailability, its solubility, its stability in solution and/or the manufacture of the drug.

In the present invention, "pharmaceutically acceptable carrier" means any compound known by a person skilled in the art for use in medicinal products. It can be, for example, compounds cited in the work Pharmacie galénique of A. LEHIR (publ. Masson, 1992 (6th edition)) (Ref 7).

In the present invention, "association" means a covalent bond with the carrier, binding by ionic interactions, the presence of the carrier and of the peptide of the invention in a solution.

The medicinal product comprising the peptide of sequence SEQ ID NO 1 can be formulated in any form permitting its administration to a patient or to an animal. It can be, for example, a formulation permitting administration by the oral, intravenous, peridural, cutaneous, or transdermal route.

In the present invention, "formulation" means an injectable formulation (for example as for OCTAPLEX (registered trademark) or SYNERGON (registered trademark)), an oral formulation, for example a syrup, a powder (for example as for OCTAPLEX (registered trademark)), granules, a tablet (for example for ESTIMA (registered trademark), a film-coated tablet (for example for PROVAMES (registered trademark)), a capsule, a spray, a local formulation, for example a cream (for example for the cream TROPICRÉME (registered trademark)), a lotion, a gel, an ocular formulation for example an eyewash, a formulation for intravenous injection, a formulation injectable by auto-injectors of the insulin pen type, a transdermal patch, tablets available per os, a formulation for sublingual ingestion, or a formulation for peridural injection.

For example, it can also be the various pharmaceutical formulations described in the work Pharmacie galénique of A. LEHIR (Publ. Masson, 1992 (6th edition)) (Ref 7).

The drug can, for example, be administered in the form of capsules, tablets, patches, injectable solutions, suppositories and/or powders.

The concentration of the peptide of the invention in the drug and/or veterinary product can be any concentration that is effective from the pharmaceutical standpoint and acceptable by the patient or the animal being treated, for example between 1 nM and 1000 nM.

The drug comprising the peptide of the invention is preferably administered in order to obtain an intravenous concentration permitting a biological effect. This effective plasma concentration can also be determined, for example by monitoring the half-life of the peptide of the invention after administration thereof by intravenous injection to a mammal and measurement of its concentration by mass spectrometry. The half-life corresponds to the time required for the concentration of said medicinal product to become equal to half the initial concentration.

The drug and/or veterinary product comprising the peptide of sequence SEQ ID NO 1 can be packaged for administration once daily, twice daily, three times a day, every other day, every three days, once a week.

The method of administration and the amount administered can be adjusted for each individual and can be determined by the practitioner notably in relation to the physiological characteristics of the individual being treated.

In the present invention, the drug can be a product for treating pain, migraine, epilepsy, Parkinson's disease, thalamic dysrhythmias, disorders of sleep and of vigilance, bipolar disorders, cardiovascular disorders (cardiac hypertrophy, hypertension), pathologies associated with aldosterone release, erectile dysfunctions, and cancerous pathologies.

Preferably, the drug of the present invention is a product for the treatment of pain, for example an analgesic, an antiallodynic agent.

Preferably, the medicinal product and/or veterinary product of the present invention is an analgesic.

The present invention also relates to a method of synthesis of the peptide of sequence YCQKFLWTCDSERPC-CEGLVCRLWCKIN (SEQ ID NO 1).

The method of synthesis in the present invention can be a method of chemical synthesis on a solid substrate or a synthesis by genetic recombination.

The method of synthesis by genetic recombination can use an expression system or a vector as defined above.

The method of synthesis of the peptide of the invention by genetic recombination can notably comprise the following steps:
- transforming a host cell with an expression vector comprising a nucleic acid sequence coding for the peptide of the invention,
- cultivating the transformed host cell in culture conditions such that it manufactures the peptide of the invention from said expression vector, and
- recovering said peptide manufactured by the host cell.

The steps of transformation, culture, and isolation of the peptide can be performed by the usual techniques of genetic recombination, for example the techniques described in the document Sambrook, Fritsch and Maniatis, "Molecular cloning, A laboratory manual", second edition, Cold Spring Harbor Laboratory Press, 1989 (Ref 3).

For example, the peptide of sequence SEQ ID NO 1 can be prepared by the classical techniques of solid-phase chemical synthesis, for example according to the methodology of Fmoc peptide synthesis on a solid substrate ("Fmoc solid phase peptide synthesis, a practical approach", by W. C. Chan and P. D. White, Oxford University Press, 2000 (Ref 4)).

Other characteristics and advantages of the invention will become apparent on reading the description given below, referring to the appended drawings.

BRIEF DESCRIPTION OF THE DRAWINGS

FIG. 5: sequence of the pT7-7 plasmid (SEQ ID NO 4).

FIG. 6A & 6B: sequence of the plasmid of the pGEX series (SEQ ID NO 5).

FIG. 7A, 7B & 7C: sequence of the plasmid of the pET32 series (SEQ ID NO 6).

FIG. 8 is a diagram showing the percentage inhibition of the current generated by the $Ca_V3.2$ channels as a function of the concentration of the toxin. The ordinate shows the percentage inhibition of the current generated by the $Ca_V3.2$ channels and the abscissa shows the decimal logarithm of the molar concentration of the toxin. The curve with the filled circles corresponds to the inhibition curve with toxin Psp3Tx1, the curve with the open circles corresponds to the inhibition curve with the synthetic toxin.

EXAMPLES

Example 1

Figure 1:
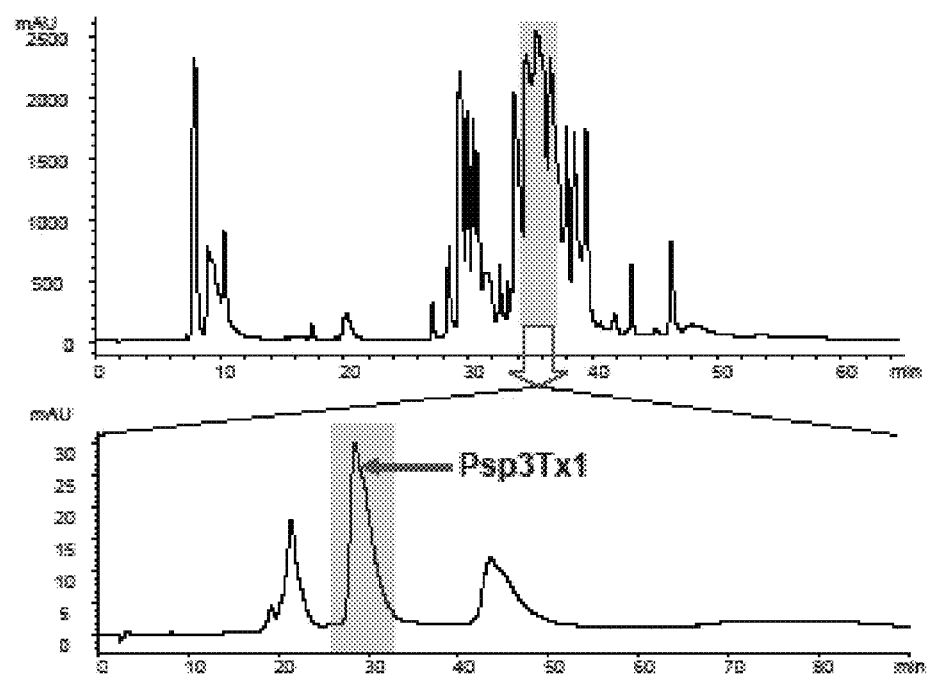
FIG. 1 is a diagram showing the profile of high-performance liquid chromatography (HPLC) of the venom of Psp3 (reversed-phase column) (top part), expressed in mAU as a function of time. The bottom diagram shows the profile of HPLC chromatography (ion-exchange column) of the fractions indicated by the gray-shaded part on the top diagram. The gray-shaded part on the lower HPLC profile corresponds to a pure peak containing the Psp3Tx1 toxin.

Characterization of the Peptide of the Invention

The PARAPHYSA SP3 venom was diluted to 1000th in the extracellular solution used for patch clamp analysis. This solution has the following composition (in mM): NaCl 135, TEACl 20, HEPES 10, $CaCl_2$ 2, $MgCl_2$ 1 (pH 7.3 with TEAOH).

HEK293 cells were transfected with a pcDNA3 expression plasmid containing the complementary DNA of the human calcium channel Cav3.2 and a reporter gene (CD8) using the jetPEI™ reagent (distributed by the company Q-biogen). After 48 hours of expression, the transfected cells were dispersed with the aid of trypsin and were then seeded at low density on culture dishes for patch clamp analysis.

The positively transfected cells were identified by means of magnetic beads covered with an anti-CD8 antibody (Dynal) as described previously in Jimenez, C., Bourinet, E., Leuranguer, V., Richard, S., Snutch, T. P. and Nargeot, J. (2000) "Determinants of voltage-dependent inactivation affect Mibefradil block of calcium channels." Neuropharmacology, 39, 1-10 (Ref 2). The electrophysiological recordings are made by the "patch clamp" technique in "whole cell" configuration by means of an Axopatch200B amplifier controlled by a Digidata interface and pClamp9 software (Molecular Devices). The extracellular recording solution containing 2 mM calcium is described above. The recordings are made using borosilicate pipettes (Sutter Instruments) stretched to have a resistance from 1.5 to 2.5 mΩ. The intrapipette solution used for the recordings has the following composition: CsCl 130 mM, HEPES 10 mM, EGTA 10 mM, $CaCl_2$ 2 mM, $MgCl_2$ 1 mM, MgATP 4 mM, TrisGTP 0.3 mM (pH 7.3 with NaOH). The results are analyzed using CLAMPFIT (registered trademark), EXCEL (registered trademark) and GRAPHPAD PRISM (registered trademark) software.

The equipment used in this example for the electrophysiological recordings is the Axopatch200B Amplifier (Molecular Devices), Digidata 1300 (Molecular Devices), pClamp9 software (Molecular Devices), the GeneClamp500 amplifier (Molecular Devices), the Olympus IX70 inverted microscope (Olympus France), the Sutter micromanipulator (Sutter Instruments). The compounds, reagents, and cells used were obtained, for the chemicals, from the company Sigma-Aldrich France, the cells used were HEK293 cells (ATCC), the beads Dynal anti-CD8 from the company Invitrogen France, the reagent JETPEI (registered trademark) from the company Q-biogen France, the microorganism *Xenopus laevis* (CRBM-CNRS Montpellier France).

For visualizing the T-type calcium currents generated by the recombinant $Ca_V3.2$ channels expressed in the transfected cells, the following protocol of stimulation with is used: starting from a rest potential of −100 mV, a depolarization of 100 ms at a potential of −30 mV is applied every 10 seconds. The amplitude of the current generated by this stimulation is measured in the control condition and then during application of the PARAPHYSA SP3 venom. For this, the PARAPHYSA SP3 venom is aspirated into a pipette identical to the recording pipette. This pipette containing the venom is connected to a pneumatic pressure system, which allows 1 to 2 microliters of venom to be applied near the cell being recorded.

Characterization of the fractions of PARAPHYSA SP3 venom is carried out in a different expression system. The cDNA coding for human Cav3.2 is injected into oocytes of *Xenopus* (*Xenopus laevis*) as described in Altier, C., Dubel, S. J., Barrére, C., Jarvis, S. E., Stotz, S. C., Spaetgens, R. L., Scott, J. D., Cornet, V., De Waard, M., Zamponi, G. W., Nargeot, J. and Bourinet, E. (2002) "Trafficking of L-type calcium channels mediated by postsynaptic scaffolding protein AKAP79." J. Biol. Chem., 277, 33598-33603 (Ref 5) and in Dubel, S. J., Altier, C., Chaumont, S., Lory, P., Bourinet, E. and Nargeot, J. (2004) "Plasma Membrane Expression of T-type Calcium Channel {alpha}1 Subunits Is Modulated by High Voltage-activated Auxiliary Subunits." J Biol Chem, 279, 29263-29269 (Ref 6). The currents are recorded by the technique of imposed voltage by double microelectrode using a GENECLAMP500 amplifier (registered trademark) (MOLECULAR DEVICES (registered trademark)) controlled by the PCLAMP9 software (registered trademark). The various chromatographic fractions obtained from the venom are dissolved in the extracellular solution containing (in mM): 5 $BaOH_2$, 25 TEAOH, 25 NaOH, 2 CsOH, 30 NMDG, 5 HEPES (pH adjusted to 7.3 with methanesulfonic acid). The recordings are made in a 15 µl microcell. The fractions (10 µl) are applied manually, directly on the oocyte recorded by means of a pipette.

Figure 2:
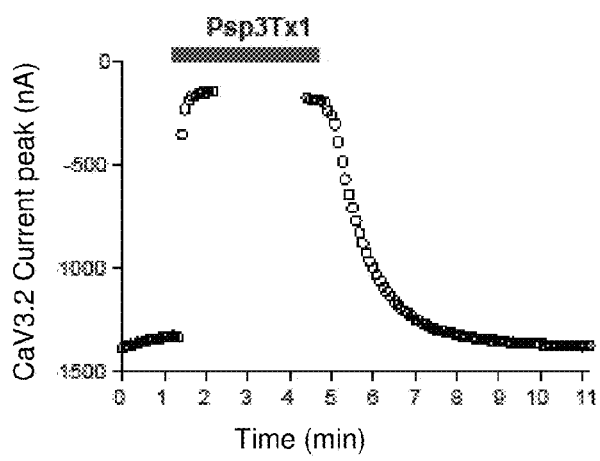
FIG. 2 is a diagram showing the current generated by the $Ca_V3.2$ channels in nano-amperes (nA) as a function of time. The curve shows the effect of application of a part of Psp3Tx1 purified by HPLC shown in FIG. 1 on the activity of the $Ca_V3.2$ channel expressed in oocytes of *Xenopus*. The current is recorded in a solution containing 5 mM barium as charge carrier and it is produced by depolarization at −30 mV starting from a rest potential of −100 mV.
Figure 3:
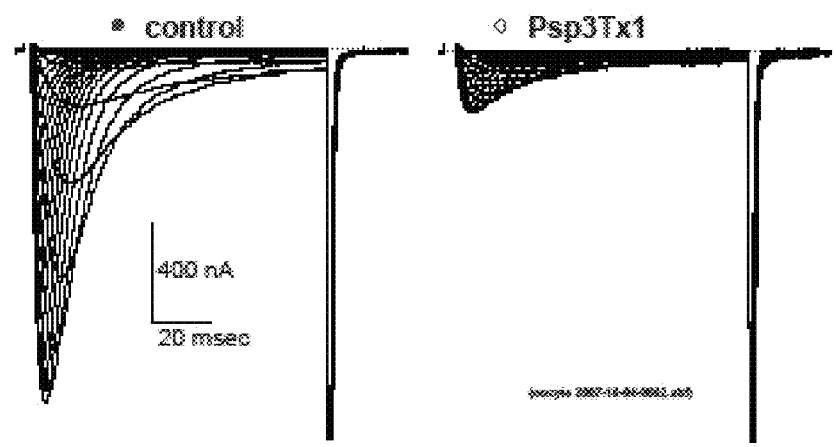
FIG. 3 is a diagram showing several recordings of currents in nano-amperes as a function of time of T-types generated by the CaV3.2 subunit at several potentials before (control) and during application of Psp3Tx1 (Psp3TX1).

Following application of the purified toxin, the current of the Cav3.2 channel is strongly inhibited after 30 seconds (FIG. 2). During washing of the effect of the toxin, recovery of the amplitude of the initial current is obtained after some minutes.

Figure 4:
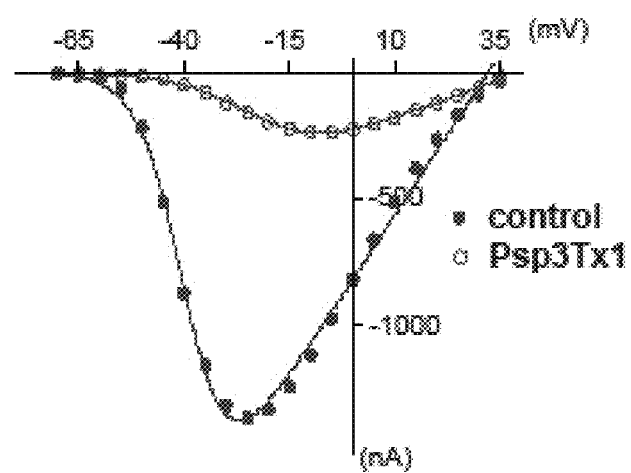
FIG. 4 is a diagram showing current-voltage relations for the recordings shown in FIG. 3. The abscissa represents the current in nano-amperes as a function of the voltage in millivolts (mV).

Moreover, as shown in FIG. 4, application of the extract causes a shift of about 20 mV toward the positive voltages of the current-voltage relation. This shift is a characteristic of toxins causing inhibition of the "voltage sensor" of ion channels. This classical effect of spider venoms is described in Winterfield J R, Swartz K J. (2000) A hot spot for the interaction of gating modifier toxins with voltage-dependent ion channels. J Gen Physiol, 116 (5):637-44.) (Ref 10). It is a blocking of the part of the channel that detects change of potential (the "voltage sensor"). The consequence is that opening of the channel is made more difficult and requires greater depolarization. The current-voltage relation is thus displaced toward more-positive potentials.

It is therefore clear that the extract comprises an antagonist of a T-type channel. This molecule is therefore a novel molecule making it possible to inhibit the painful signal.

Example 2

Isolation and Sequencing of the Peptide of the Invention

The venom fractions inhibiting calcium channel activity as presented in the preceding example were isolated and investigation for the component responsible for this inhibition was carried out by successive steps of tests of activity coupled with steps of fractionation.

The PARAPHYSA SP venom was obtained by electrical stimulation of the chelicerae of adult females. The venom was collected in microtubes, and lyophilized.

Preparation of the venom for the analyses of activity and for chromatographic separation consisted of dissolving the lyophilizate in ultrapure water to a dilution 10 times that of the initial volume of venom, centrifugation (14,000 revolutions per minute, 20 min) and filtreiton on a 0.45 µm membrane (SJHVL04NS MILLIPORE (registered trademark)).

Purification of the active component of the venom by chromatography: In a first step, an aliquot of 100 µl of the venom dilution (10 µl equivalents of raw venom) is fractionated by reversed-phase high-performance liquid chromatography (RP-HPLC) on a C8 semi-preparative column (5C8MS, 10×250 mm, Waters). The gradient used is composed of water+0.1% trifluoroacetic acid (A)/acetonitrile+0.1% trifluoroacetic acid (B). The gradient is programmed as follows: 0% B for 5 min, 0 to 60% B in 60 min, 60 to 90% B in 10 min, flow 2 mL/min. The fractions are collected manually at column exit, monitoring the variation of UV absorbance at 215 nm. These fractions are lyophilized and then their activity is tested on the T-type calcium channel as described above.

A second purification step is performed as follows, on the active fractions from RP-HPLC: these fractions are analyzed in a second step of cation-exchange chromatography, on a TOSOH SP5PW column (registered trademark) (4.6×70 mm) (Tosoh), with a linear gradient of ammonium acetate in water (from 20 mM to 1M in 50 min) with a flow of 0.5 mL/min. The fractions collected are lyophilized and then their activity is tested on the T-type calcium channel as described above.

After identification of the active fraction, the purity and the molecular weight of the peptide constituting the active fraction are determined by MALDI-TOF (Matrix-Assisted Laser Desorption/Ionization Time-Of-Flight) mass spectrometry.

The mass spectrometry measurements are performed by MALDI-TOF mass spectrometry on a VOYAGER DE-PRO (registered trademark) mass spectrometer (Applied Biosystems (registered trademark)) in reflection mode. The peptides are mixed with the α-cyano-4-hydroxycinnamic acid matrix (α-CHCA, SIGMA (registered trademark), 5 mg/mL in 50:50:0.1 water:acetonitrile:TFA) and analyzed. The mass spectra are calibrated with internal standards and analyzed using the DATA EXPLORER software (registered trademark).

The sequence of the purified peptide is determined by automatic sequencing using a gas-phase sequencer (Applied Biosystems Procise) by Edman degradation.

Prior to analysis, the disulfide bridges of the purified peptide are reduced by DTT (dithiothreitol 10 mM, 55° C., 45 min) and alkylated with IAA (iodoacetic acid, 50 mM, at 20° C., 30 min) according to a protocol known by a person skilled in the art (see John M. Walker. The Protein Protocols Handbook, Humana Press 1996 (ISBN 0-89603-339-2) (Ref 14). The reduced/alkylated peptide is submitted to a desalting by RP-HPLC C18 chromatography on a Merck CHROMOLITH SPEEDROD (registered trademark) column (0.46×50 mm). The sequence of the reduced/alkylated peptide is then determined by automatic gas-phase N-terminal sequencing on a peptide sequencer of model BIOSYSTEMS 477A (registered trademark) (BIOSYSTEMS (registered trademark)).

The peptide sequence obtained is YCQKFLWTCDSERPCCEGLVCRLWCKIN (SEQ ID NO 1)

This example therefore clearly demonstrates that the T-type channel antagonist molecule is the peptide of sequence ID No. 1.

This peptide therefore represents a novel molecule for inhibiting the painful signal.

Example 3

Chemical Synthesis of the Peptide of Sequence SEQ ID NO 1

The company ALTERGEN (registered trademark) synthesizes the peptide of the invention chemically according to the following protocol: solid-phase synthesis according to the Merifield technique, Fmoc strategy.

The inhibitory activity of the peptide identified in example 2 has been tested in vitro on various T-type calcium channels (results not supplied).

Example 4

Chemical Synthesis of the Peptide of Sequence SEQ ID NO 1

The company GENEPEP (registered trademark) synthesized the peptide of the invention chemically according to the following protocol: solid-phase synthesis according to the Merifield technique, Fmoc strategy.
(Ref 4)

The company SYNPROSIS (registered trademark) folded the linear peptide produced by the company Genepep according to the following protocol: incubation of 10 μM of the linear peptide Psp3-Tx1 in a buffer containing 1 mM of reduced glutathione (GSH), 1 mM of oxidized glutathione (GSSG), 100 mM of trishydroxymethylaminomethane (TRIS) pH9, 25% glycerol. Incubation was carried out for 24 hours with gentle agitation at room temperature. The synthetic toxin Psp3-Tx1 was purified by reversed-phase HPLC chromatography on an RP-C18 CHROMOLITH (registered trademark) column using a gradient from 10 to 50% of acetonitrile (ACN) in a 0.1% solution of trifluoroacetate (TFA).

The mass of the folded synthetic peptide was verified by mass spectrometry, giving a value of 3398.0 dalton (Da) in agreement with the formation of the 3 disulfide bridges between the 6 cysteines.

Example 5

Characterization of the Synthetic Peptide of the Invention Produced in Example 4

The inhibitory activity of the synthetic peptide from example 4 was tested in vitro on the $Ca_V3.2$ channel. Inhibition with the natural peptide (Psp3-Tx1) was compared in the same conditions. The synthetic peptide and the natural peptide (natural toxin) were diluted to a stock concentration of $10^{-3}$ molar in distilled water. Starting from this stock concentration, the peptides were diluted in a solution corresponding to the extracellular solution used for the patch clamp analysis. This solution has the following composition (in mM): NaCl 135, TEACl 20, HEPES 10, $CaCl_2$ 2, $MgCl_2$ 1 (pH 7.3 with TEAOH). The concentrations tested were as follows: for the synthetic peptide: $10^{-8}$, $10^{-7}$, and $10^{-6}$ molar; for the natural peptide: $10^{-9}$, $10^{-8}$, $3.10^{-8}$, $10^{-7}$, $3.10^{-7}$, and $10^{-6}$ molar.

HEK293 cells (ATCC) stably expressing the complementary DNA sequence of the human Cav3.2 calcium channel were used. At each passage of the cell line, cells were seeded at low density on culture dishes for "patch clamp" analysis (molecular electrophysiology).

The cells positively transfected were identified by means of magnetic beads covered with an anti-CD8 antibody (Dynal) as described previously in Jimenez, C., Bourinet, E., Leuranguer, V., Richard, S., Snutch, T. P. and Nargeot, J. (2000) "Determinants of voltage-dependent inactivation affect Mibefradil block of calcium channels." *Neuropharmacology*, 39, 1-10 (Ref 2).

The electrophysiological recordings were made by the "patch clamp" technique in the "whole cell" configuration using an Axopatch200B amplifier controlled by a Digidata interface and the pClamp10 software (Molecular Devices). The extracellular recording solution containing 2 mM calcium is described above.

The recordings were made using borosilicate pipettes (Sutter Instruments) stretched so as to have a resistance from 1.5 to 2.5 mΩ.

The intrapipette solution used for the recordings has the following composition: CsCl 130 mM, HEPES 10 mM, EGTA 10 mM, $CaCl_2$ 2 mM, $MgCl_2$ 1 mM, MgATP 4 mM, TrisGTP 0.3 mM (pH 7.3 with NaOH). The results are analyzed using CLAMPFIT (registered trademark), EXCEL (registered trademark) and GRAPHPAD (registered trademark) software.

The equipment used in this example for the electrophysiological recordings is the Axopatch200B Amplifier (Molecular Devices), Digidata 1440 (Molecular Devices), pClamp10 software (Molecular Devices), the GeneClamp500 amplifier (Molecular Devices), Olympus IX70 inverted microscope (Olympus France), the Sutter micromanipulator (Sutter Instruments). The compounds, reagents, and cells used were obtained, for the chemicals, from the company Sigma-Aldrich France, the cells used were HEK293 cells (ATCC), the beads were Dynal anti-CD8 from the company Invitrogen France, the JETPEI reagent (registered trademark) was from the company Q-biogen France.

For visualizing the T-type calcium currents generated by the $Ca_V3.2$ recombinant channels expressed in the transfected cells, the following protocol of stimulation with is used: starting from a rest potential of −100 mV, a depolarization of 100 ms at a potential of −30 mV is applied every 10 seconds.

The amplitude of the current generated by this stimulation is measured in the control condition and then during application of increasing concentrations of the synthetic peptide from example 4, or of increasing concentrations of the native toxin Psp3-Tx1. For this, solutions containing different concentrations of the synthetic peptide or of toxin Psp3-Tx1 are distributed into infusion tubes connected to a collector for applying these various solutions near the cell being recorded.

The inhibitory activity of each concentration of the synthetic peptide or of the native toxin is thus determined by measuring the amplitude of the CaV3.2 current of the recorded cell at the plateau of the effect.

The inhibitory effects of the synthetic peptide and of the natural peptide were presented in the form of percentage blocking at each concentration for constructing "dose-effect" curves shown in FIG. 8. These "dose-effect" curves were analyzed with GRAPHPAD PRISM (registered trademark) software with the sigma analysis function "log(antagonist) vs. response—variable slope" for calculating the dose inhibiting 50% of the current (EC50) as well as slope of the corresponding curve or Hill number.

FIG. 8 shows the dose-response curves for the natural peptide (Psp3Tx1) (curve with filled black circles) and the synthetic peptide (curve with open black circles).

Thus, in FIG. 8, EC50 for the natural toxin is 1.1 μM with a Hill number of 0.87 (the number of cells analyzed is 6), and the EC50 for the synthetic peptide is 2.01 μM with a Hill number of 0.89 (number of cells analyzed equal to 20).

The results therefore show that the synthetic peptide and the native peptide inhibit the currents of the $Ca_V3.2$ channel.

The results are described with a Hill coefficient equal to about 1, implying 1:1 interaction between the channel and the peptides.

This example therefore clearly demonstrates that peptide of sequence ID NO 1, extracted from spider venom as presented in example 1 and/or synthesized chemically, inhibits the currents of the $Ca_T3.2$ channel.

Example 6

Analgesic Effect of the Peptide of the Invention

Mice are used for observing the analgesic effect of the peptide of the invention with respect to pain induced by thermal stimuli.

The mice are C57BL/6J wild-type mice and C57BL/6J CaV3.2−/− mice. The total number of mice is 10 wild-type and 10 CaV3.2−/−.

Two groups of mice (C57BL/6J) are used, one group injected intrathecally with a physiological solution comprising the peptide of the invention at a concentration of 10 and 100 nM and a second group (control group) receiving only intrathecal injection of physiological solution alone. The mice are then submitted to the test of immersion of the tail in a water bath at 46° C. The purpose of this experiment is to determine the time after which the mice react to the painful heat, thus showing the threshold of appearance of the painful signal connected with perception of heat. The same experiment is conducted in parallel on two other groups of C57BL/6J mice lacking the gene coding for the T-type calcium channel encoded by the CaV3.2 subunit. The purpose of this experiment is to show the selectivity of the peptide of the invention.

The results show a significant difference in time to react to heat between the group of mice injected with the peptide and the control group of mice. The time to react to heat is significantly longer in the mice that receive the peptide of sequence SEQ ID NO 1.

Mice are used for observing the analgesic effect of the peptide of the invention with respect to mechanical stimuli.

The mice are C57BL/6J wild-type mice and C57BL/6J CaV3.2−/− mice. The total number of mice is 10 wild-type and 10 CaV3.2−/−.

Two groups of mice (C57BL/6J) are used, one group injected intrathecally with a physiological solution comprising the peptide of the invention at a concentration of 10 and 100 nM and a second group (control group) only receiving intrathecal injection of the physiological solution alone. The mice are then submitted to the mechanical stimulation test with von Frey bristles. The purpose of this experiment is to determine the threshold of reaction to a mechanical stimulus of increasing intensity applied on the arch of the foot. The animals' reaction threshold is correlated with the appearance of the painful signal connected with the perception of mechanical pressure. The same experiment is conducted in parallel on two other groups of C57BL/6J mice lacking the gene coding for the T-type calcium channel encoded by the CaV3.2 subunit. The purpose of this experiment is to show the selectivity of the peptide of the invention.

The results show a significant difference in threshold of perception of mechanical pressure between the group of mice injected with the peptide and the control group of mice. The pressure threshold is significantly higher in the mice that receive the peptide of sequence SEQ ID NO 1.

The peptide of the invention therefore has an expected analgesic effect with respect to thermal and mechanical painful stimuli.

This example therefore demonstrates that the peptide of sequence SEQ ID NO 1, identified in example 2, is a novel molecule for the treatment of pain.

Example 7

Comparison of the Analgesic Effect of the Peptide of the Invention with that of a Reference Analgesic The mice and the experimental protocol used in the present example are identical to those described in example 4.

Two additional groups of mice are tested:
a group injected intrathecally with a dose of morphine (1 µg/kg), and
a group in which the peptide of sequence SEQ ID NO 1 was (10 nM).

Example 8

Antihypertensive Effect of the Peptide of the Invention

The mice used in the present example are identical to those described in example 4.

Mice are used in order to observe the antihypertensive effect of the peptide of the invention. Two groups of mice (C57BL/6J) are used, one group injected intravenously with a physiological solution comprising the peptide of the invention at a concentration of 10 and 100 nM and a second group (control group) receiving only intravenous injection of physiological solution alone. The blood pressure is measured by the principle of the caudal sleeve method (Plehm, R., Barbosa, M. E. and Bader, M. (2006) Animal models for hypertension/blood pressure recording. *Methods Mol Med*, 129, (Ref 15)).

Example 9

Antiproliferative Effect of the Peptide of the Invention

LNCAP prostate cancer cells are used in order to observe the antiproliferative effect of the peptide of the invention.

The culture medium used is RPMI 1640 medium (Bio-Whittaker S A, Verviers, Belgium), supplemented with 5 mM L-glutamine (Sigma-Aldrich, L'Isle d'Abeau, France) and 10% FBS (Applera France S A, Courtaboeuf, France) as stated in the document of Gackiere F, Bidaux G, Delcourt P, Van Coppenolle F, Katsogiannou M, Dewailly E, Bavencoffe A, Van Chuoï-Mariot M T, Mauroy B, Prevarskaya N, Mariot P. (2008) CaV3.2 T-type calcium channels are involved in calcium-dependent secretion of neuroendocrine prostate cancer cells. J Biol Chem, 283 (15):10162-73.
(Ref 16)

Two conditions of cells are used:
one condition in which the cells are cultured in different assays in the presence of the peptide of the invention at concentrations of 10, 30, 100, 300, 1000 nM, and
a second condition (control) without peptide.

Cellular proliferation is measured by the CELLTRACE method (registered trademark) CFSE (INVITROGEN (registered trademark)) based on incorporation of the CFSE fluorescent tracer by the cultured cells and measurement of the labeled cells using a flow cytometer.

LIST OF REFERENCES

Ref 1 Bourinet, E., et al., Silencing of the CaV3.2 T-type calcium channel gene in sensory neurons demonstrates its major role in nociception. Embo J, 2005. 24(2): p. 315-24.

Ref 2 Jimenez, C., Bourinet, E., Leuranguer, V., Richard, S., Snutch, T. P. and Nargeot, J. (2000) Determinants of voltage-dependent inactivation affect Mibefradil block of calcium channels. *Neuropharmacology,* 39, 1-10.

Ref 3 Sambrook, Fritsch and Maniatis, Molecular cloning, A laboratory manual, second edition, Cold spring Harbor Laboratory Press, 1989

Ref 4 Fmoc solid Phase peptide synthesis, a practical approach>>, published by W. C. Chan et P. D. White, Oxford university press, 2000

Ref 5 Altier, C., Dubel, S. J., Barrère, C., Jarvis, S. E., Stotz, S. C., Spaetgens, R. L., Scott, J. D., Cornet, V., De Waard, M., Zamponi, G. W., Nargeot, J. and Bourinet, E. (2002) Trafficking of L-type calcium channels mediated by the postsynaptic scaffolding protein AKAP79. *J. Biol. Chem.,* 277, 33598-33603.

Ref 6 Dubel, S. J., Altier, C., Chaumont, S., Lory, P., Bourinet, E. and Nargeot, J. (2004) Plasma Membrane Expression of T-type Calcium Channel {alpha}1 Subunits Is Modulated by High Voltage-activated Auxiliary Subunits. *J Biol Chem,* 279, 29263-29269.

Ref 7 Pharmacie galénique de A. LEHIR (Ed. Masson, 1992 (6th edition)

Ref 8 Taylor, J. T., Zeng, X. B., Pottle, J. E., Lee, K., Wang, A. R., Yi, S. G., Scruggs, J. A., Sikka, S. S. and Li, M. (2008) Calcium signaling and T-type calcium channels in cancer cell cycling. *World J Gastroenterol,* 14, 4984-4991.

Ref 9 Chen, C. C., Lamping, K. G., Nuno, D. W., Barresi, R., Prouty, S. J., Lavoie, J. L., Cribbs, L. L., England, S. K., Sigmund, C. D., Weiss, R. M., Williamson, R. A., Hill, J. A. and Campbell, K. P. (2003) Abnormal coronary function in mice deficient in alpha1H T-type Ca2+ channels. *Science,* 302, 1416-1418.

Ref 10 Winterfield J R, Swartz K J. (2000) A hot spot for the interaction of gating modifier toxins with voltage-dependent ion channels. J Gen Physiol, 116(5):637-44.)

Ref 11 Panner A, Cribbs L L, Zainelli G M, Origitano T C, Singh S, Wurster R D. (2005) Variation of T-type calcium channel protein expression affects cell division of cultured tumor cells. Cell Calcium, 37(2):105-19

Ref 12 Lu F, Chen H, Zhou C, Liu S, Guo M, Chen P, Zhuang H, Xie D, Wu S. (2008) T-type Ca2+ channel expression in human esophageal carcinomas: a functional role in proliferation Cell Calcium. 43(1):49-58

Ref 13 Taylor J T, Huang L, Pottle J E, Liu K, Yang Y, Zeng X, Keyser B M, Agrawal K C, Hansen J B, Li M (2008) Selective blockade of T-type Ca2+ channels suppresses human breast cancer cell proliferation. Cancer Lett, 18; 267(1):116-24

Ref 14 John M. Walker. The Protein Protocols Handbook, Humana Press 1996 (ISBN 0-89603-339-2)

Ref 15 Plehm, R., Barbosa, M. E. and Bader, M. (2006) Animal models for hypertension/blood pressure recording. *Methods Mol Med,* 129

Ref 16 Gackière F, Bidaux G, Delcourt P, Van Coppenolle F, Katsogiannou M, Dewailly E, Bavencoffe A, Van Chuoï-Mariot M T, Mauroy B, Prevarskaya N, Mariot P. (2008) CaV3.2 T-type calcium channels are involved in calcium-dependent secretion of neuroendocrine prostate cancer cells. J Biol Chem, 283 (15):10162-73.

Ref 17 Han K K, Martinage A (1992) Post-translational chemical modification(s) of proteins. Int J Biochem. 24(1): 19-28.; Walsh G, Jefferis R (2006) Post-translational modifications in the context of therapeutic proteins *Nature Biotechnology*—24, 1241-1252

Ref 18 Escoubas P. (2006) Molecular diversification in spider venoms: a web of combinatorial peptide libraries. Mol Divers. 10(4):545-54).

The invention claimed is:

1. An isolated peptide comprising the amino acid sequence YCQKFLWTCDSERPCCEGLVCRLWCKIN (SEQ ID NO: 1).

2. An antagonist of a T-type calcium channel comprising the peptide according to claim 1.

3. The antagonist according to claim 2, wherein said calcium channel is at least one of the Cav3.2 channel and the Cav3.1 channel.

4. A drug composition comprising the peptide according to claim 1 and a carrier.

5. The drug composition according to claim 4, wherein said drug composition is an analgesic.

6. A method of synthesis of the peptide of claim 1, comprising a step of chemical synthesis on a solid substrate or a step of synthesis by genetic recombination.

7. The isolated peptide according to claim 1, wherein the peptide comprises an L amino acid, a D amino acid or a combination of L and D amino acids.

8. The isolated peptide according to claim 1, wherein the peptide comprises a pseudopeptide bond between two amino acids.

9. The isolated peptide according to claim 1, wherein the peptide comprises a modification at the N-terminal end, the C-terminal end, or both the N-terminal and C-terminal ends.

10. The isolated peptide according to claim 1, wherein the peptide comprises a modified amino acid or a non-natural amino acid.

11. The isolated peptide according to claim 1, wherein the peptide is a cyclic peptide.

12. An isolated peptide consisting of the amino acid sequence YCQKFLWTCDSERPCCEGLVCRLWCKIN (SEQ ID NO: 1).

* * * * *

UNITED STATES PATENT AND TRADEMARK OFFICE
CERTIFICATE OF CORRECTION

PATENT NO.         : 8,664,179 B2                                                           Page 1 of 1
APPLICATION NO.    : 13/144734
DATED              : March 4, 2014
INVENTOR(S)        : Bourinet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Twenty-ninth Day of September, 2015

Michelle K. Lee
*Director of the United States Patent and Trademark Office*